(12) United States Patent
Aime et al.

(10) Patent No.: US 7,780,952 B2
(45) Date of Patent: Aug. 24, 2010

(54) AGENTS FOR MAGNETIC IMAGING METHOD

(75) Inventors: Silvio Aime, Carignano (IT); Valentina Mainero, Ivrea (IT); Simonetta Chirich Geninatti, Turin (IT); Claudia Cabella, Pecco (IT)

(73) Assignee: Bracco Imaging SpA, Milan (IT)

( * ) Notice: Subject to any disclaimer, the term of this patent is extended or adjusted under 35 U.S.C. 154(b) by 1275 days.

(21) Appl. No.: 10/516,781

(22) PCT Filed: Jun. 2, 2003

(86) PCT No.: PCT/EP03/05761

§ 371 (c)(1),
(2), (4) Date: Dec. 3, 2004

(87) PCT Pub. No.: WO03/103722

PCT Pub. Date: Dec. 18, 2003

(65) Prior Publication Data
US 2005/0175543 A1 Aug. 11, 2005

(30) Foreign Application Priority Data
Jun. 5, 2002 (EP) .................................. 02012531

(51) Int. Cl.
A61B 5/055 (2006.01)
(52) U.S. Cl. ...................... 424/9.3; 424/1.11; 424/1.65; 424/1.69; 424/9.1
(58) Field of Classification Search ............... 424/1.11, 424/1.65, 1.69, 9.1, 9.3, 9.32, 9.36, 9.321, 424/9.322, 9.323, 9.34, 9.35, 9.361, 9.362, 424/9.363, 9.364, 9.365, 9.37; 534/7, 10–16
See application file for complete search history.

(56) References Cited

U.S. PATENT DOCUMENTS

| 4,622,420 | A | | 11/1986 | Meares et al. |
| 4,822,594 | A | | 4/1989 | Gibby |
| 5,330,743 | A | | 7/1994 | Gibby et al. |
| 5,620,675 | A | * | 4/1997 | McBride et al. ............ 424/1.69 |
| 6,719,958 | B1 | * | 4/2004 | Gozzini et al. ............ 424/9.363 |

FOREIGN PATENT DOCUMENTS

| AU | 81780/94 B | 7/1995 |
| AU | 199856554 B2 | 6/1998 |
| EP | 1199312 A2 | 4/2002 |
| JP | 05-503104 A | 5/1993 |
| JP | 07/502725 A | 3/1995 |
| JP | 07-224050 A | 8/1995 |
| JP | 07/509467 A | 10/1995 |
| JP | 07-330773 A | 12/1995 |
| JP | 2000-506152 A | 5/2000 |
| JP | 2001/504843 A | 4/2001 |
| JP | 2001-522348 A | 11/2001 |
| JP | 2001-523650 A | 11/2001 |
| JP | 2002-511845 A | 4/2002 |
| JP | 2002-515462 A | 5/2002 |
| WO | 93/03351 A1 | 2/1992 |
| WO | 92/04919 A1 | 4/1992 |
| WO | 94/02068 A1 | 2/1994 |
| WO | WO 94 02068 A | 2/1994 |
| WO | WO 95/14492 * | 6/1995 |
| WO | 97/32862 A1 | 9/1997 |
| WO | 98/05626 A1 | 2/1998 |
| WO | 98/47541 A1 | 10/1998 |
| WO | WO 98 47541 | 10/1998 |
| WO | 99/25389 A2 | 5/1999 |
| WO | 99/59640 A2 | 11/1999 |
| WO | WO 99/59640 A2 | 11/1999 |
| WO | WO 99/59640 A3 | 11/1999 |

OTHER PUBLICATIONS

Lawaczeck R. et al; "Gadolinium Neutron Capture Therapy (GDNCT) With MRI Contrast Media In Vitro Studies" Cancer Neutron Capture Therapy, XX, XX, 1996 pp. 859-864, XP000951499.
PCT Search Report for PCT/EP03/05761, mail date Sep. 22, 2003.
Lawaczeck R. et al; "Gadolinium Neutron Capture Therapy (GDNCT) With MRI Contrast Media In Vitro Studies" Cancer Neutron Capture Therapy, 1996 pp. 859-864, XP000951499, Pleneum Press, New York.

* cited by examiner

*Primary Examiner*—D L Jones
(74) *Attorney, Agent, or Firm*—M. Caragh Noone

(57) ABSTRACT

The invention provides MRI detectable species of formula (I): $D_p\text{-}S_n\text{-}N_m$, wherein D is a MRI detectable moiety; S is a spacer; N is a molecule of a nutrient or pseudo-nutrient; n is 0 or an integer, m is an integer and p is an integer. These compounds are useful for internalizing into tumor cells an amount of the MRI detectable moiety that is distinguishably higher than the amount internalized in normal healthy cells thus allowing the diagnosis of tumors. The internalization of the MRI detectable moiety involves the nutrients or pseudo-nutrients transporting system. Preferred compounds of formula (I) are those wherein D is the chelated complex of a paramagnetic metal ion.

12 Claims, 6 Drawing Sheets

AGENTS FOR MAGNETIC IMAGING METHOD

The present invention relates to new MRI detectable species suitable for use as contrast agents in a magnetic imaging method, and to the injectable compositions containing them for the magnetic resonance imaging (MRI) of living subjects and for the diagnosing of tumors.

The invention also refers to the injectable compositions of some of said new MRI detectable species for the therapy of tumors.

Finally the present invention also relates to the new intermediates in the preparation of the new MRI detectable species of the invention.

BACKGROUND OF THE INVENTION

Magnetic resonance imaging (MRI) is a nuclear magnetic resonance technique that is used clinically to distinguish between different tissues or organs in the human or animal body through the spatial localization of water protons in the tissues or organs. The signal that is obtained by this technique and is then converted into an imaging depends in fact on the water proton concentrations and on the relaxation rates within the different types of tissues.

MRI often requires the use of contrast agents, i.e. agents that influence the local relaxation behaviour of the observed nuclei in certain tissues or organs, because if MRI is performed without employing a contrast agent, differentiation of the tissue of interest from the surrounding tissues in the resulting image may be difficult.

The in vivo utilization of paramagnetic complexes as non-specific agents for contrast enhanced MRI has been the subject of a number of different studies. Paramagnetic contrast agents involve materials which contain unpaired electrons. The unpaired electrons act as small magnets within the main magnetic field to increase the rate of longitudinal ($T_1$) and transverse ($T_2$) relaxation. Generally, paramagnetic contrast agents are used for their ability to decrease $T_1$ (positive contrast agents) and in use they enhance image intensity from the regions to which they distribute.

Paramagnetic contrast agents typically comprise metal ions, such as for instance transition metal ions, which provide a source of unpaired electrons. Particularly preferred and therefore studied in more depth, resulted to be $Gd^{3+}$ (with 7 unpaired electrons) and $Mn^{2+}$ (with 5 unpaired electrons). Particular attention has been paid to the $Gd^{3+}$ ion as this ion shows a very high magnetic moment coupled to a relaxation rate relatively long at the magnetic fields of interest in the MR area (in the range of nanoseconds). However these metal ions are also generally highly toxic or at least poorly tolerated and need to be strongly coordinated with a ligand that occupies the major number of coordination sites. Generally speaking, to control toxicity and at the same time get a sufficient contrast in the imaging, it is necessary to have paramagnetic complexes endowed with high thermodynamic and kinetic stability, containing at least one molecule of water directly coordinated to the metal ion in rapid exchange with the "bulk" water.

The first contrast agent for MRI approved by the Regulatory Authorities was GdDTPA (Magnevist®, by Schering AG), followed by GdDOTA (Dotarem®, by Guerbet SA), GdDTPA-BMA (Omniscan®, by Nycomed Imaging AS), and GdHPDO3A (ProHance®, by Bracco Imaging S.p.A.). The chemical formula of these contrast agents is reported hereinbelow:

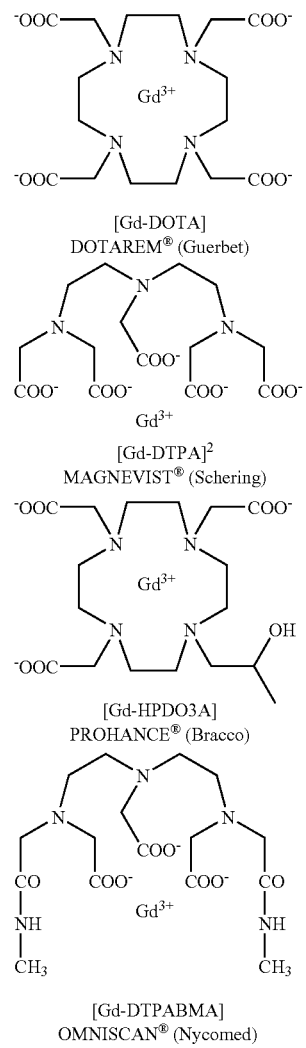

[Gd-DOTA]
DOTAREM® (Guerbet)

[Gd-DTPA]²
MAGNEVIST® (Schering)

[Gd-HPDO3A]
PROHANCE® (Bracco)

[Gd-DTPABMA]
OMNISCAN® (Nycomed)

These four contrast agents share some similar pharmacological features as they all diffuse from plasma into the extracellular fluids and are excreted through the kidney via glomerular filtration. They are particularly useful for the diagnosis of hematoencephalic barrier lesions.

Linked thereto are other two Gd(III) complexes that are used in the imaging of the liver: Gd EOB-DTPA (Eovist®, by Shering AG) and Gd BOPTA (MultiHance®, by Bracco Imaging S.p.A.) (the chemical formula of the two ligands, EOB-DTPA and BOPTA, is reported below)

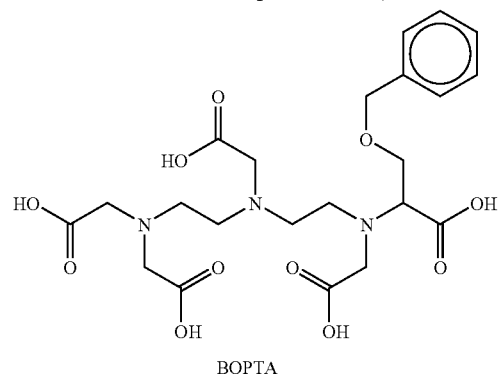

BOPTA

-continued

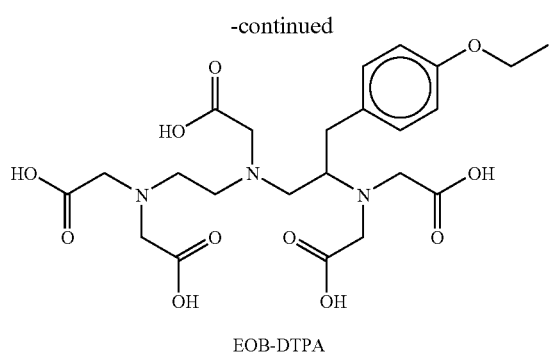

EOB-DTPA

These two compounds are characterised by an increased lipophilic behaviour due to the introduction of an aromatic substituent in the ligand structure and for this reason are preferably uptaken by the liver cells.

Another class of compounds useful as contrast agents for MRI are ferromagnetic materials which are employed for their ability to decrease $T_2$. Ferromagnetic materials have high, positive magnetic susceptibilities and maintain their magnetism in the absence of an applied field. Ferromagnetic materials for use as MRI contrast agents are for instance described in WO 86/01112 and WO 85/043301.

A third class of magnetic materials that can be used in MRI are those generally indicated as superparamagnetic materials. Analogously to paramagnetic materials, the superparamagnetic ones do not maintain their magnetism in the absence of an externally applied magnetic field. Superparamagnetic materials can have magnetic susceptibilities nearly as high as ferromagnetic materials and higher than the paramagnetic ones. As generally used, also superparamagnetic materials alter the MR image by decreasing $T_2$ and therefore result in a darkening of the tissues or fluids where they are present or accumulate versus the lighter background where they are not present.

Iron oxides such as magnetite and gamma ferric oxide exhibit ferrromagnetism or superparamagnetism depending on the size of the crystals comprising the material, with larger crystals (typically with an average size larger than 0.3 µM) being ferromagnetic.

The general idea of an MRI enhancing contrast agent comprising a moiety that is detectable in a magnetic resonance imaging procedure linked to a molecule capable of specific binding to a cellular receptor is already known.

See for instance U.S. Pat. No. 4,827,945 that discloses i.a. coated magnetite particles for use as MRI contrast agents, said particles being surrounded by a polymer to which biologically active molecules, chosen to target specific organs or tissues, may be attached.

See also WO 01/30398 and the literature cited therein where the use of receptor-binding ligands bound to a paramagnetic chelate is described.

The idea is that since there are specific receptors which are known to be overexpressed in the cells of certain tumors, being able to selectively distinguish a tumor cell from a normal cell will allow to visualize and identify precise locations of the tumor masses and better manage the disease.

The paramagnetic, ferromagnetic or superparamagnetic compounds containing the suitably selected targeting moiety (e.g. antibody, antibody fragment, peptide, protein, and the like) bind to the relevant receptors on the surface of the tumor cells to be targeted and is possibly internalised. The number of receptors per cell however is generally lower than the number of MRI detectable metal ions required to have a MR signal visible with the actual MRI technologies. To increase the contrast and make the signal more visible it is therefore necessary to increase the concentration of the contrast agent in the cell or on the surface of the cell. This can be obtained either giving to the cell sufficient time to internalize the label/targeting compound (so that the signal can be given by the contrast agent inside the cell as well as around or on the surface of the cell) and/or administering simultaneously a compound capable to increase internalization of the receptor-binding compound, or increasing the number of MRI detectable metal units linked to the targeting moiety (via dendrimers or multimers). In the latter case, particularly useful is the internalization route based on receptor mediated (fluid) endocytosis that allows the entrapment of a huge number of paramagnetic units.

While theoretically excellent, in practice neither of these approaches has led to a commercial product yet. On the one hand, in fact, once the targeting MRI detectable compound is bound to the cell surface, it is not always possible to achieve or induce the desired internalization and on the other hand the use of large multimers is generally connected with an unacceptable increase in toxicity of the product because of the large molecular weight thus obtained.

For utility in diagnostic imaging the optimum contrast agent should provide a contrast sufficient to clearly distinguish between normal, healthy cells and tumor cells using the available equipment and without creating any toxicity problem.

SUMMARY OF THE INVENTION

In one aspect, the present invention provides new compounds suitable for use in the manufacture of contrast agents, said compounds containing an MRI detectable moiety and being functionalised in such a way to be easily internalised into the cells.

More particularly the present invention provides for a MRI detectable species that is useful for internalising into tumor cells an amount of a MRI detectable metal that is distinguishably higher than the amount internalised in normal healthy cells.

It has now been found in fact that it is possible to distinguish between tumor cells and normal cells using contrast agents based on a MRI detectable species that contain at least one MRI detectable moiety that is bound, either directly or through a spacer, to at least one molecule of a nutrient or pseudo-nutrient. The nutrient or pseudo-nutrient transporters or transporting systems that are present into the human body, will in fact recognize the nutrient or pseudo-nutrient molecule and will carry it, together with the at least one MRI detectable moiety that is linked thereto, into the cells where said MRI detectable moiety or moieties will thus concentrate to provide a more evident visualization of the cell. The altered metabolism of the tumor cells that require a much higher amount of nutrients or pseudo-nutrients or that selectively employ certain specific pseudo-nutrients, will allow a clear distinction between tumor and normal cells as the former ones will internalise a much higher amount of the compounds containing a MRI detectable moiety.

In another aspect, the present invention provides a pharmaceutical composition comprising an effective amount of a MRI detectable species of the invention together with at least one pharmaceutically acceptable carrier. In a preferred embodiment said pharmaceutical composition will be in the form of an injectable composition.

Said injectable composition can be employed for diagnostic purpose using the MRI technology to visualize tumor cells and, when in the new compounds the MRI detectable moiety is a chelated complex of a paramagnetic metal.

In still a further aspect the present invention also relates to a process for the preparation of the new compounds by conjugating the MRI detectable moiety D or a precursor thereof with the nutrient or pseudo-nutrient molecule, either directly or through a spacer, and to the new intermediates obtained therein.

DETAILED DESCRIPTION OF THE INVENTION

Figure 1:
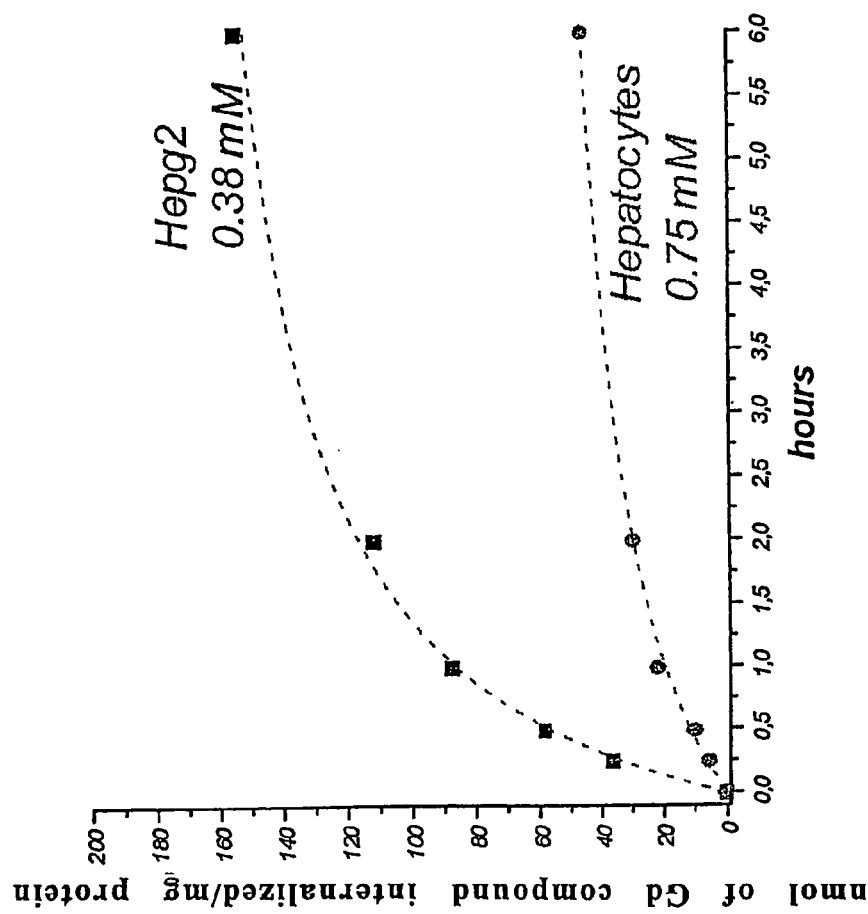
FIG. 1 reports the differential uptake of the compound of Example 1 by a human hepatoma cell line with respect to hepatocytes FIG. 2 reports the differential uptake of the compound of Example 3 by a human hepatoma cell line with respect to hepatocytes FIG. 3 summarises the differential uptake of the compound of Example 3 by various cancer cell lines.

More particularly a first object of the present invention is a MRI detectable species of following formula (I)

$$D_p\text{-}S_n\text{-}N_m \quad (I)$$

wherein
D is a MRI detectable moiety
S is a spacer
N is a molecule of a nutrient or pseudo-nutrient
n is 0 or an integer
m is an integer and
p is an integer.

The MRI detectable species of formula (I) must contain at least one MRI detectable moiety D and at least one nutrient or pseudo-nutrient molecule N bound together.

If in the above formula (I) m is 1 and p is 1, then D and N can be bound together either directly (n=0) or through a spacer S (n=1).

It is also possible to have, in the above formula (I), one MRI detectable moiety D bound to more than one nutrient or pseudo-nutrient molecule N, either directly or through a number of spacers S which may be up to the number of nutrient or pseudo-nutrient molecules N (i.e., p=1, m>1, n=0 or an integer $\leq$m). In such a case typically the number of nutrient or pseudo-nutrient molecules will be up to 5, preferably up to 4, more preferably up to 3 and even more preferably up to 2.

The MRI detectable species (I) may also contain more than one, and typically up to 10, preferably up to 8, more preferably up to 6, and even more preferably up to 4, MRI detectable moieties D, that can be linked to one molecule of nutrient or pseudo-nutrient N, either directly or through one or up to an even number of spacers S (i.e., p>1, n$\leq$p, m=1). In case the more than one MRI detectable moieties D are linked to the N molecule through one spacer S, said spacer will preferably contain a multiplicity of binding sites equal to the number of MRI detectable moieties D, i.e., the spacer S will provide the backbone on which several D moieties or a cluster of D moieties are bound.

When the MRI detectable species of formula (I) contains more than one MRI detectable moiety D, said moieties can also be bound to more than one nutrient or pseudo-nutrient molecule N through a spacer S containing a multiplicity of binding sites (i.e., p>1, n=1, m>1.

In the formula (I) above therefore p typically will be an integer of from 1 to 10, preferably of from 1 to 8, more preferably of from 1 to 6, and even more preferably of from 1 to 4, i.e., 1, 2, 3 or 4; n is typically 0 or an integer of from 1 to 5, preferably 0, or an integer of from 1 to 3, more preferably 0 or an integer of from 1 to 2, and even more preferably 0 or 1; and m is typically an integer of from 1 to 5, preferably of from 1 to 4, more preferably of from 1 to 3, and even more preferably 1 or 2.

While generally the MRI detectable species of the present invention can be represented as a characterizable compound of formula (I) as indicated above, there may be instances where the MRI detectable species according to the present invention can only be represented as a combination of moieties (D and N and optionally S) bonded or otherwise associated, e.g. conjugated, with each other. As used herein however the term "MRI detectable species of formula (I)" will include also these compositions of matter.

In formula (I) above D is any MRI detectable moiety, i.e. any moiety which affects local electromagnetic fields (i.e. any paramagnetic, superparamagnetic or ferromagnetic species), that contains at least one portion capable of being linked to at least one molecule of nutrient or pseudo-nutrient N, either directly or through a spacer S.

The MRI detectable moiety D therefore can be a coated ferromagnetic particle, a coated superparamagnetic particle or a chelated complex of a paramagnetic metal ion wherein the coating of the ferromagnetic or superparamagnetic particles or the chelator of the paramagnetic metal contain at least one site for a possible link to a spacer S or to a nutrient/pseudo-nutrient molecule N.

Examples of suitably coated ferromagnetic or superparamagnetic particles are for instance those described in U.S. Pat. Nos. 4,770,183, 4,827,945, 5,707,877, 6,123,920, and 6,207,134 where the coating materials, i.e., polymers such as polysaccharides, carbohydrates, polypeptides, organosilanes, proteins, and the like, gelatin-aminodextran, or starch and polyalkylene oxides, can be functionalised to allow binding of the particle to the spacer or to the nutrient/pseudo-nutrient molecule.

In a preferred embodiment of the present invention however the MRI detectable moiety D is a paramagnetic metal ion complexed with a chelating ligand L.

Preferred paramagnetic metal ions include ions of transition and lanthanide metals (i.e. metals having atomic number of 21 to 29, 42, 43, 44, or 57 to 71). In particular ions of Mn, Fe, Co, Ni, Eu, Gd, Dy, Tm, and Yb are preferred, with those of Mn, Fe, Eu, Gd, and Dy being more preferred and Gd being the most preferred.

As known in the art and used herein, the term "chelator" or "chelating ligand" is intended to refer to a compound containing donor atoms that can combine by coordinative bonding with a metal atom to form a cyclic structure (coordination cage) called "chelation complex" or "chelate".

Suitable chelating ligands L that are or can be functionalised in such a way to allow binding of the paramagnetic chelation complex D to the spacer or nutrient/pseudo-nutrient molecule as in formula (I) above, include the residue of a polyaminopolycarboxylic acid, either linear or cyclic, in racemic or optically active form, such as ethylenediaminotetracetic acid (EDTA), diethylenetriaminopentaacetic acid (DTPA), N-[2-[bis(carboxymethyl)amino]-3-(4-ethoxyphenyl)propyl]-N-[2-[bis(carboxymethyl)amino]ethyl]-L-glycine (EOB-DTPA), N,N-bis[2-[bis(carboxymethyl)amino] ethyl]-L-glutamic acid (DTPA-GLU), N,N-Bis[2-[bis(carboxymethyl)amino]ethyl]-L-γ-glutamyl-L-glutamine, N,N-bis[2-[bis(carboxymethyl)amino]ethyl]-L-lysine (DTPA-LYS), the DTPA mono- or bis-amide derivatives, such as N,N-bis[2-[carboxymethyl[(methylcarbamoyl)methyl]amino]ethyl]glycine (DTPA-BMA), 4-carboxy-5,8,11-tris(carboxymethyl)-1-phenyl-2-oxa-5,8,11-triazatridecan-13-oic acid (BOPTA), 1,4,7,10-tetraazacyclododecan-1,4,7,10-tetraacetic acid (DOTA), 1,4,7,10-tetraazacyclododecan-1,4,7-triacetic acid (DO3A), 10-(2-hydroxypropyl)-1,4,7,10-tetraazacyclododecan-1,4,7-triacetic acid (HPDO3A), 2-methyl-1,4,7,10-tetraazacyclododecan-1,4,7,10-tetraacetic acid (MCTA), (α,α',α",α'")-tetramethyl-1,4,7,10-tetraazacyclododecan-1,4,7,10-tetraacetic acid (DOT MA), 3,6,9,15-tetaazabicyclo[9.3.1]pentadeca-1(15),11,13-triene-3,6,9-triacetic acid (PCT A), [4-(1,6,10-triazaundecan)-phenyl-aminocarbonylmethyl]-1,4,7,10-tetraazacyclododecan 4,7,10-triacetic acid or of a derivative thereof wherein one or more of the carboxylic groups are in the form of the corresponding salts, esters, or amides; or of a corresponding compound wherein one or more of the carboxylic groups is replaced by a phosphonic and/or phosphinic group, such as for instance 4-carboxy-5,11-bis(carboxymethyl)-1-phenyl-12-[(phenylmethoxy)methyl]-8-(phosphonomethyl)-2-oxa-5,8,11-triazatridecan-13-oic acid, N,N'-[(phosphonomethylimino)di-2,1-ethanediyl]bis[N-(carboxymethyl)glycine], N,N'-[(phosphonomethylimino)di-2,1-ethanediyl]bis[N-(phosphonomethyl)glycine)], N,N'-[(phosphinomethylimino)di-2,1-ethanediyl]bis[N-(carboxymethyl)glycine], 1,4,7,10-tetrazacyclododecane-1,4,7,10-tetrakis[methylen(methylphosphonic)]acid, or 1,4,7,10-tetraazacyclododecane-1,4,7,10-tetrakis[methylen(methylphosphinic)]acid.

Suitable chelating ligands L as well as the processes for their preparation are described for instance in the following patents: GB-A-2,137,612, EP-A-230,893, EP-A-255,471, EP-A-299,795, EP-A-325,762, EP-A-565,930, EP-A-594,734, U.S. Pat. No. 4,885,363, EP-A-773,936, WO-A-9426313, WO-A-9426754, WO-A-9426755, WO-A-9519347, WO-A-9731005, WO-A-9805625, WO-A-9805626, WO-A-9935133, WO-A-9935134, and WO-A-0146207, which are incorporated herein by reference.

Preferred chelating ligands L are linear and macrocyclic polyaminopolycarboxylic acids, in racemic or optically active form.

More preferred are ethylenediaminotetracetic acid (EDTA), diethylenetriaminopentaacetic acid (DTPA), N-[2-[bis(carboxymethyl)amino]-3-(4-ethoxyphenyl)propyl]-N-[2-[bis(carboxymethyl)amino]ethyl]-L-glycine (EOB-DTPA), N,N-bis[2-[bis(carboxymethyl)amino]ethyl]-L-glutamic acid (DTPA-GLU), N,N-Bis[2-[bis(carboxymethyl)amino]ethyl]-L-γ-glutamyl-L-glutamine, N,N-bis[2-[bis(carboxymethyl)amino]ethyl]-L-lysine (DPTA-LYS), N,N-bis[2-(carboxymethyl[(methylcarbamoyl)methyl]amino)ethyl]glycine (DTPA-BMA), 4-carboxy-5,8,11-tris(carboxymethyl)-1-phenyl-2-oxa-5,8,11-triazatridecan-13-oic acid (BOPTA), 1,4,7,10-tetraazacyclododecan-1,4,7,10-tetraacetic acid (DOTA), 1,4,7,10-tetraazacyclododecan-1,4,7-triacetic acid (DO3A), 10-(2-hydroxypropyl)-1,4,7,10-tetraazacyclododecan-1,4,7-triacetic acid (HPDO3A), 2-methyl-1,4,7,10-tetraazacyclododecan-1,4,7,10-tetraacetic acid (MCTA), (α,α',α",α'")-tetramethyl-1,4,7,10-tetraazacyclododecan-1,4,7,10-tetraacetic acid (DOT MA), 3,6,9,15-tetraazabicyclo[9.3.1]pentadeca-1(15),11,13-triene-3,6,9-triacetic acid (PC TA), [4-(1,6,10-triazaundecan)-phenyl-aminocarbonylmethyl]-1,4,7,10-tetraazacyclododecan-4,7,10-triacetic acid and the derivatives thereof wherein one or more of the carboxylic groups are in the form of the corresponding alkali metal, alkaline earth metal, or quaternary ammonium salts, ($C_1$-$C_4$)alkyl esters or unsubstituted, mono- or di-substituted amides.

Most preferred are ethylenediaminotetracetic acid (EDTA), diethylenetriaminopentaacetic acid (DTPA), 4-carboxy-5,8,11-tris(carboxymethyl)-1-phenyl-2-oxa-5,8,11-triazatridecan-13-oic acid (BOPTA), 1,4,7,10-tetraazacyclododecan-1,4,7,10-tetraacetic acid (DO TA), 1,4,7,10-tetraazacyclododecan-1,4,7-triacetic acid (DO3A), and 10-(2-hydroxypropyl)-1,4,7,10-tetraazacyclododecan-1,4,7-triacetic acid (HPDO3A), (α,α',α",α'")tetramethyl-1,4,7,10-tetraazacyclododecan-1,4,7,10-tetraacetic acid (DOTMA), as well as the analogs thereof where the methyl groups are replaced by higher alkyl homologs, 3,6,9,15-tetraazabicyclo[9.3.1]pentadeca-1(15),11,13-triene-3,6,9-triacetic acid (PCTA) and [4-(1,6,10-triazaundecan)-phenyl-aminocarbonylmethyl]-1,4,7,10-tetraazacyclododecan-4,7,10-triacetic acid.

As used herein the term "nutrient" refers to any substance or compound that is essential for sustaining the cell life in the organism concerned, while the term "pseudo-nutrient" refers to any substance or compound that is nonessential during health but is required in the diet in certain pathophysiologic states because cell utilisation exceeds the capacity for endogenous biosynthesis or to any substance or compound that is capable of being utilised by the cells in any of their vital functions or as an assimilable source of nutrients.

Examples of "nutrients" are typically monosaccharides and the essential amino acids. The term "monosaccharides" includes glucose, which is the most preferred one, fructose and other hexoses. The term "essential amino-acid" generally refers to the L-isomers of the α-amino acids which are found in nature.

Typical examples of "pseudo-nutrients" are the polyamines, the derivatives of the essential amino acids and the non-essential amino-acids.

Examples of polyamines are e.g. putrescine, spermidine, and spermine, that are present in all the cells and play an important role in several essential cell functions through their interaction with DNA, RNA, proteins, and lipids. The uptake of these compounds by the rapidly growing cells as well as by the tumor cells is known to be very high.

A suitable example of essential amino-acid derivative suitable as pseudo-nutrients is e.g. agmatine, the compound obtainable by decarboxylation of arginine, that can be used by the cell as a nitrogen source and is known to be internalised by the cells through the same transport system used for polyamines.

Non essential amino-acids are e.g. the D-isomers of the natural essential amino-acids, any mixture of the L- and D-isomers, as well as synthetic α-amino acids which are not found in nature. An example of molecule suitable as pseudo-nutrient is glutamine that is not an essential amino-acid but becomes a conditionally essential amino acid in the host with cancer. Glutamine in fact is known to be the main source of nitrogen for tumor cells that compete with the host for circulating glutamine.

Other substances or compounds not specifically listed above may however be employed as the nutrient or pseudo-nutrient molecule. More particularly any substance or compound that is recognized by at least one transporting system of the living organism that receives the MRI detectable species (I) and that is internalised by the tumor cells in a higher amount with respect to the normal healthy cells, can suitably be employed.

Since there are several different transporting systems that are known to preferentially transport one or the other nutrient or pseudo-nutrient molecule into the cell of a given tissue or organ, it would thus be possible also to specifically design the type of nutrient or pseudo-nutrient to be coupled with the MRI detectable moiety D in such a way to preferentially direct the MRI detectable species (I) to the target cells.

Examples of known transporting systems are for instance the ASC system that is expressed by different types of cells, that typically transports neutral apolar or neutral polar amino-acids, such as alanine, leucine, valine, methionine, serine, cysteine, glutamine, threonine, asparagine; the N system that specifically transports amino-acids that contains nitrogen in the side chain, such as glutamine, asparagine and histidine; the $B^{0,+}$ system that transports also cationic amino-acids and is expressed only in certain organs, i.e. lung and trachea; the $Y^+$ system that is ubiquitous with the only exception of epatocytes and mediates the uptake of cationic amino-acids as well as that of glutamine; the L system for the transport of neutral apolar amino-acids, such as leucine, isoleucine, valine, phenylalanine, tyrosine, tryptophane, methionine, and of some neutral polar amino-acids, such as glutamine, serine and threonine; the T system that preferentially transports neutral aromatic amino-acids; and the various families of glucose transporters, GLUT1, GLUT2, GLUT3, GLUT4, and GLUT5, which are expressed in the various tissues and are responsible for the cellular uptake of glucose and the other hexoses.

When more than one molecule of nutrient or pseudo-nutrient N is present, each N can be independently selected among the nutrient and pseudo-nutrient molecules as indicated above. In a preferred embodiment however when more than one molecule N is linked to the MRI detectable moiety D, all the N molecules are of the same compound or substance.

As indicated above, in the case of nutrients, saccharides and essential amino acids are the preferred molecules, wherein the most preferred ones are glucose, neutral amino acids such as alanine and phenylalanine, and cationic amino acids such as lysine and arginine.

In case of pseudo-nutrients, polyamines such as putrescine and spermidine, non essential amino-acids, such as glutamine and essential amino acid derivatives such as agmatine are the most preferred compounds.

Each of the molecules of nutrient or pseudo-nutrient N can be linked to the MRI detectable moiety D either directly or through a spacer S.

When the MRI detectable moiety D is linked to a nutrient or pseudo-nutrient N through a direct bond, said bond usually involves interaction between functional groups located on the nutrient molecule N and on the MRI detectable moiety, i.e. on the coating of the ferromagnetic or superparamagnetic particle or—in the preferred embodiment of the present invention according to which D is a paramagnetic chelated complex—on the chelating ligand L. In general, non limitative examples of chemically reactive functional groups which may be employed to this purpose include amino, hydroxy, thiol, carboxy, carbonyl and the like groups.

In the preferred embodiment where the MRI detectable moiety D is a paramagnetic metal ion complexed with a chelating ligand L, the chelating ligand L may be attached directly to the nutrient or pseudo-nutrient molecule N via one of the metal coordinating groups of the chelant which may form an ester, amide, thioester, or thioamide bond with an amine, thiol, or hydroxy group present on the N molecule. In such a case preferably the ligand L will contain free carboxyl groups, and a direct covalent bond with the nutrient or pseudo-nutrient molecule N can be obtained through formation of an ester or, preferably, an amide bond with respectively a hydroxy or amino group possibly present in the N molecule. Alternatively, or additionally, the N molecule and the chelating ligand L may be directly linked via a functionality attached to the chelant L backbone, and in such a case it is also possible to devise a ligand L bearing as a substituent in its backbone e.g. the residue of an amino-acid or amino-acid derivative, a polyamine, or a glucose molecule N.

Alternatively to the direct joining of the MRI detectable moiety D to the nutrient or pseudo-nutrient molecule N, these two elements can also be connected through a homo- or hetero-bifunctional linker, i.e. a spacer S. In this case said spacer S will contain at least two specific reactive moieties separated by a spacing arm, wherein one of the reactive moieties will provide for a covalent bonding with the MRI detectable moiety D and the other with the nutrient or pseudo-nutrient molecule N. The spacing arm may typically consist of an alkylidene, alkenylidene, alkynylidene, cycloalkylidene, arylidene, or aralkylidene radical that can be substituted and be interrupted by heteroatoms such as oxygen, nitrogen, and sulphur. In a preferred embodiment said spacer arm consists of an aliphatic, straight or branched chain, that effectively separates the reactive moieties of the spacer so that ideally the spatial configuration of the molecule of nutrient or pseudo-nutrient N is not influenced by the presence of the MRI detectable moiety D and the molecule of nutrient or pseudo-nutrient N is thus more easily recognized by the transporter. Said chain may be interrupted by groups such as, —O—, —S—, —CO—, —NR—, —CS— and the like groups or by aromatic rings such as phenylene radicals, and may bear substituents such as —OR, —SR, —NRR$_1$, —COOR, —CONRR$_1$, and the like substituents, wherein R and R$_1$, each independently, may be a hydrogen atom or an organic group.

The reactive moieties in said bifunctional spacer, that may be the same or, preferably, different, need to be capable of reaction with the functional groups present in the MRI detectable moiety D and in the nutrient or pseudo-nutrient molecule N, i.e. need to be able to react with carboxyl, amino, hydroxyl, sulphydryl, carbonyl, and the like groups.

Examples of functional groups capable of reaction with carboxylic groups include diazo compounds such as diazoacetate esters and diazoacetamides, which-react with high specificity to generate ester groups. Carboxylic acid modifying reagents such as carbodiimides, e.g. 1-cyclohexyl-3-(2-morpholinyl-4-ethyl)carbodiimide (CMC) and 1-ethyl-3-(3-dimethylaminopropyl)carbodiimide (EDC), may also be usefully employed. Other useful carboxylic acid modifying reagents include isoxazolium derivatives, chloroformates, and N-carbalkoxydihydroquinolines. Examples of reactive moieties capable of reaction with sulphydryl groups include α-haloacetyl compounds and maleimide derivatives. Examples of reactive moieties capable of reaction with amino groups include alkylating and acylating agents. Representative of the alkylating agents are α-haloacetyl compounds, maleimide derivatives, reactive aryl halides and alkyl halides, α-haloalkyl ethers, aldehydes and ketones capable of Schiff's base formation with amino groups (the adducts formed usually being stabilised through reduction to give a stable amine), epoxide derivatives, such as epichlorohydrin and bisoxiranes. Examples of acylating agents include isocyanates and isothiocyanates, acid anhydrides, acid halides, active esters, and those useful reagents for amide bond formation widely known and conventionally used for peptide syntheses.

Said spacer may also contain more than two functional groups. In particular when a single spacer molecule S is used to bind more than one MRI detectable moiety D to one or more than one nutrient or pseudo-nutrient molecule N or vice-versa, said spacer may contain a multiplicity of possible binding sites or be a molecular aggregate with a multiplicity of built-in or pendant groups which bind covalently or non-covalently (.g. coordinatively) with the MRI detectable moieties D and the nutrient or pseudo-nutrient molecules N in such a way to anchor said moieties thereto with a strength and for a time sufficient to bring the MRI detectable species (I) into the cells.

The nature of the spacer S may have a critical bearing on the stability of the end MRI detectable species and on the capability for the transporting systems to recognize the nutrient or pseudo-nutrient molecule. As indicated in fact it should bind the MRI detectable moiety D to the recognized nutrient or pseudo-nutrient molecule N for an adequate period of time that would allow the MRI detectable moiety D to be internalised by the tumor cells in an amount sufficient to give a clearly distinguishable contrast imaging. It should also bind the MRI detectable moiety D to the nutrient or pseudo-nutrient molecule in a way that would ensure an appropriate spatial conformation that allows the nutrient or pseudo-nutrient molecule to be easily recognized by the transport system. In a preferred embodiment it should also be biodegradable, i.e. contain a bond that may be susceptible to an enzymatic or a chemical cleavage, particularly once it has been transported into the cell. Furthermore, when according to the preferred embodiment of the invention the MRI detectable moiety D is a paramagnetic metal chelated complex, said optional spacer S should also ensure that water molecules may have access to the chelated paramagnetic ion (as the entity of the signal will depend on the rate of exchange of the water molecule of the coordination cage with the water bulk).

When more than one molecule of spacer S is present, each of them can be independently selected as indicated above. According to a preferred embodiment, however, in such a case all the n molecules of spacer S are identical.

The reaction conditions used for obtaining the MRI detectable species (I) will vary depending on the particular type of reactive moieties employed but are analogous to those known in the literature for similar general reactions and can be easily devised by any skilled technician.

In general for the preparation of the MRI detectable species (I), it is possible to conjugate first the spacer, if any, with the nutrient or pseudo-nutrient molecules N and then conjugate the obtained intermediate product with the MRI detectable moiety or moieties D; or alternatively, it is also possible to conjugate first the MRI detectable moiety or moieties D with the spacer or spacers, if any, and then conjugate the obtained intermediate with the nutrient or pseudo-nutrient molecule(s) N. However, when in the MRI detectable species of formula (I), D is a paramagnetic metal chelated complex, preferably the process for the preparation of these compounds will comprise conjugating one or more chelating ligands L to one or more nutrient or pseudo-nutrient molecules N either directly or through one or more spacers S, by any suitable sequence of steps, to get a suitable precursor of the desired end compound (I), said precursor having following general formula (II)

$$L_p\text{-}S_n\text{-}N_m \quad (II)$$

wherein
L is a chelating ligand
S is a spacer
N is a molecule of a nutrient or pseudo-nutrient
n is 0 or an integer
m is an integer and
p is an integer.

and then metallating the chelant groups L in said intermediate compound (II) with the suitably selected paramagnetic metal. The precursors, intermediate compounds, of formula (II), that will also be indicated herein as "functionalised chelators", represent a further specific object of the present invention In the above formula (II) the meanings of L, S, N, n, m, and p are as defined above in relation with the end compounds (I). Further objects of the present invention are the following preferred chelating ligands, according to general formula (II), as well as the processes for their preparation thereof. 6,16-dicarbonyl-5,8,11,14,17-pentaaza-8,11,14-tricarboxymethyl-heneicosandiguadinine, 6,16-dicarbonyl-5,19-dicarboxy-5,8,11,14,17-pentaaza-8,11,14-tricarboxymethyl-heneicosandioic acid diamide, 3,6,9-triaza-3,6,9-tricarboxymethylundecanoic acid bis-glucopyranosylamide, 2,24-diamino-8,18-dicarbonyl-7,10,13,16,19-pentaaza-10,13,16-tricarboxymethyl-pentaheicosandioic acid, 2,16-dibenzyl-4,13-dicarbonyl-3,6,9,12,15-pentaaza-6,9,12-tricarboxymethyl-heptadecandioic acid, 10,20-dicarbonyl-4,9,12,15,18,21,26-heptaaza-12,15,18-tricarboxymethyl-nonaheicosan-1,29-diamine, 4,26-diamino-5,10,20,25-tetracarbonyl-12,15,18-tricarboxymethyl-6,9,12,15,18,21,24-heptaaza-nonaheicosan-1,29-diguanidina; N,N-Bis[2-[bis(carboxymethyl)amino]ethyl]-L-γ-glutamyl-L-glutamine, N,N-Bis[2-[bis(carboxymethyl)amino]ethyl]-L-γ-glutamyl-agmatine, N,N-Bis[2-[bis(carboxymethyl)amino]ethyl]-L-γ-glutamyl-arginine and [4-(1,6,10-triazaundecan)-phenyl-aminocarbonylmethyl]-1,4,7,10-tetraazacyclododecan-4,7,10-triacetic acid.

Most preferred are N,N-Bis[2-[bis(carboxymethyl)amino]ethyl]-L-γ-glutamyl-L-glutamine, N,N-Bis[2-[bis(carboxymethyl)amino]ethyl]-L-γ-glutamyl-agmatine, N,N-Bis[2-[bis(carboxymethyl)amino]ethyl]-L-γ-glutamyl-arginine and [4-(1,6,10-triazaundecan)-phenyl-aminocarbonylmethyl]-1,4,7,10-tetraazacyclododecan-4,7,10-triacetic acid.

However, a further preferred embodiment of the present invention are the corresponding complexes compounds, according to general formula (I), of the above indicated list of compounds. In particular with ions of Mn, Fe, Co, Ni, Eu, Gd, Dy, Tm, and Yb are preferred, with those of Mn, Fe, Eu, Gd, and Dy and Gd being more preferred and Gd being the most preferred.

In particular the persons skilled in the art are well aware of the fact that is highly preferred to work with chelates of high thermodynamic stability in order to limit potential toxic effects associated to the release of free metal ions.

Among the methods generally known for incorporating a metal ion into a chelator, i.e. direct incorporation, template synthesis and transmetallation, the direct incorporation is the preferred one to obtain the compounds of formula (I) wherein D is a paramagnetic metal chelated complex starting from the intermediates of formula (II). Thus the MRI detectable species (I) wherein D is a paramagnetic chelated complex can be easily obtained by merely exposing or mixing an aqueous solution of the functionalized chelators (II) with a paramagnetic metal salt in an aqueous solution having a pH comprised between about 4 and about 9, and preferably comprised between about 5 and about 8. The salt can be any salt but preferably a water soluble salt of the paramagnetic metal, such as a halide. Said salts are preferably selected so as not to interfere with the binding of the metal ion with the functionalised chelator (II). The funtionalised chelator (II) is preferably in aqueous solution at a pH of between about 5 and about 8. It can be mixed with buffer salts such as citrate, acetate, phosphate and borate, to produce the optimum pH. Preferred paramagnetic metal ions include ions of transition and lanthanide metals (i.e. metals having atomic number of 21 to 29, 42, 43, 44, or 57 to 71). In particular ions of Mn, Fe, Co, Ni, Eu, Gd, Dy, Tm, and Yb are preferred, with those of Mn, Fe, Eu, Gd, and Dy being more preferred and Gd being the most preferred.

Preferably the MRI detectable species (I) wherein D is a paramagnetic chelated complex should have a zero residual charge on the coordination cage in order not to alter the residual charges possibly present on the nutrient or pseudo-nutrient moiety of the end species (I).

Preferred cations of inorganic bases suitable for salifying the paramagnetic chelated complexes, if necessary, comprise the ions of alkali metals or alkaline-earth metals such as potassium, sodium, magnesium, calcium, and the like metals, including any mixed salt. Preferred cations of organic bases suitable for this purpose comprise those obtained by protonation of primary, secondary and tertiary amines, such as ethanolamine, diethanolamine, morpholine, glucamine, N-methylglucamine, N,N-dimethylglucamine, basic amino-acids such as lysine, arginine, and ornithine, and the like organic bases.

The MRI detectable species (I) wherein D is a paramagnetic chelation complex, should contain at least one molecule of water in the coordination cage of the chelation complex so as to guarantee a rlp higher than $1\ s^{-1}mM^{-1}$. Higher relaxivities (such as higher than $4\ s^{-1}mM^{-1}$, or higher than $8\ s^{-1}mM^{-1}$, or higher than $10\ s^{-1}mM^{-1}$ or higher than $15\ s^{-1}mM^{-1}$) can be advantageous but not strictly necessary because of the high amount of internalized MRI detectable moiety D.

The MRI detectable species (I) according to the present invention may be administered to patients for imaging in an amount sufficient to give the desired contrast with the particular technique used in the MRI. Generally, dosages of from about 0.001 to about 5.0 mmoles of MRI detectable species (I) per kg of body weight are sufficient to obtain the desired contrast. For most MRI applications preferred dosages of imaging metal compound will be in the range of from 0.01 to 2.5 mmoles per kg of body weight.

The MRI detectable species (I) of the present invention can be employed for the manufacture of a contrast medium for use in a method of diagnosis by MRI involving administering said contrast medium to a human or animal being and generating an image of at least part of said human or animal being.

More particularly the MRI detectable species (I) according to the present invention can be employed for the manufacture of a contrast medium for use in a method of diagnosing tumors, said method involving administering said contrast medium to a human or animal being and detecting the major uptake of said detectable species by tumor cells with respect to normal cells.

For said use the MRI detectable species (I) of the present invention may be formulated with conventional pharmaceutical aids, such as emulsifiers, stabilisers, anti-oxidant agents, osmolality adjusting agents, buffers, pH adjusting agents, and the like agents, and may be in a form suitable for parenteral administration, e.g. for infusion or injection.

Thus the MRI detectable species (I) according to the present invention may be in conventional administration forms such as solutions, suspensions, or dispersions in physiologically acceptable carriers media, such as water for injection.

Parenterally administrable forms, e.g. i.v. solutions, should be sterile and free from physiologically unacceptable agents, and have low osmolality to minimize irritation and other adverse effects upon administration. These parenterally administrable solutions can be prepared as customarily done with injectable solutions. They may contain additives, such as anti-oxidants, stabilizers, buffers, etc., which are compatible with the chemical structure of the MRI detectable species (I) and which will not interfere with the manufacture, storage and use thereof.

Said pharmaceutical compositions may also contain suitable agents that may increase the amount of MRI detectable moiety internalised. As an example it would be possible to administer the MRI detectable species (I) in combination with a compound that specifically inhibits the enzymes responsible for the biosynthesis of the nutrient or pseudo-nutrient N within the cell. This would lead to an increased uptake of the exogenous nutrient N in the form of MRI detectable species (I). Said "internalization adjuvant" may be administered simultaneously with the MRI detectable species (I) and in such a case the formulation may contain both ingredients. Alternatively it can be administered in advance with respect to the MRI detectable species (I) and in such a case two separate formulations should be provided that may be presented in the form of a kit.

The following examples further illustrate the present invention in some representative embodiments thereof and in particular describe the preparation of some representative compounds of formula (I) and intermediates of formula (II) according to the present invention. As will be known to those of skill in the art, however, these same compounds may also be prepared following different synthetic routes.

Example 1

Preparation of the Gadolinium Complex of 6,16-dicarbonyl-5,8,11,14,17-pentaaza-8,11,14-tricarboxymethyl-heneicosandiguadinine (Gadolinium Complex of N,N'-(4-guanidinobutyl)diethylen-etriaminopentaacetic Acid bis-amide)

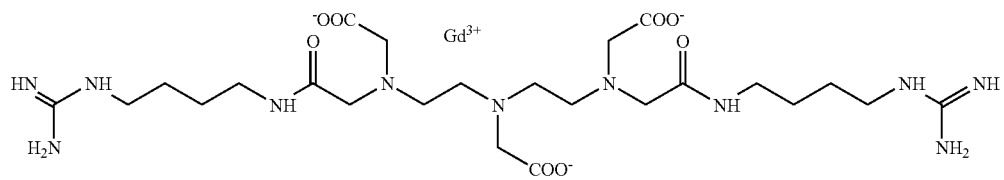

a) Preparation of Diethylenetriaminopentaacetic Acid bis-anhydride

Diethylenetriaminopentaacetic acid (10 g; 0.0255 mol) and pyridine (14.54 ml; 0.18 mol) are charged into a 100-ml reaction flask equipped with magnetic stirrer, heating oil bath, and dripping funnel. While the temperature is kept at the room value and the solution is stirred, acetic anhydride (10.56 ml; 0.11 mol) is added dropwise. The reaction mixture is heated to 65° C. for 3 hours, and then cooled to room temperature. The solid obtained is recovered by filtration on büchner, washed on filter with acetic anhydride (2×10 ml), methylene chloride (2×10 ml) and ethyl ether (2×10 ml). The white powder is then dried under vacuum yielding 8.82 g of the compound of title a) (97%).

The $^1$H-NMR, 13C-NMR, IR and MS spectra are consistent with the indicated structure.

b) Preparation of 6,16-dicarbonyl-5,8,11,14,17-pentaaza-8,11,14-tricarboxymethyl-heneicosandiguadinine A mixture of agmatine free base (3.27 g; 0.02531 mol) and DMSO (70 ml) is stirred at 50° C. for two hours. A solution of the compound obtained in step a) above (4.20 g, 0.01175 mol) in dimethylsulfoxide (DMSO) (15 ml) is added portionwise over a period of two hours and the mixture is allowed to react at 50° C. for 4 hours and then at room temperature for additional 20 hours. At the end of the reaction time the solution is clear but a lower yellow phase of a jelly consistency is present. The DMSO phase is recovered by decantation and acetone is added thereto until precipitation of a solid product is complete. The lower yellow phase is dissolved in a small amount of water and acetone is added thereto to get an additional crop of solid precipitate. The two crops are combined and washed several times with fresh acetone, left under stirring overnight. The surnatant is then removed and the solid is taken up with water, washed again with acetone, and dried yielding 8.03 g of a raw product that is dissolved in acid water (pH=2) and purified by column chromatography on Amberlite™ XAD 1180.

The $^1$H-NMR, 13C-NMR, IR and MS spectra are consistent with the indicated structure.

c) Preparation of the Gadolinium Complex of 6,16-dicarbonyl-5,8,11,14,17-pentaaza-8,11,14-tricarboxymethyl-heneicosandiguadinine An aqueous solution of the chelating ligand obtained in step b) above (7.0 g; 0.0122 mol) is brought to pH 6.5 by the addition of NaOH and an equimolar amount of GdCl$_3$ (3.22 g; 0.0122 mol) is then slowly stirred in at room temperature. During the addition the pH of the reaction mixture is monitored and adjusted to 6.5 with NaOH. Once the addition of GdCl$_3$ is over, the solution is brought to pH 8.5 and filtered on a 22 μm syringe filter. A small amount of the chelating ligand obtained in step b) above is then added to the filtrate and the pH is brought to 7. Removal of the solvent under vacuum yields the compound of the title as a white solid.

Example 2

Preparation of the Gadolinium Complex of 6,16-dicarbonyl-5,19-dicarboxy-5,8,11,14,17-pentaaza-8,11,14-tricarboxymethyl-heneicosandioic Acid Diamide (Gadolinium Complex of N,N'-glutamin-diethylenetriaminopentaacetic Acid bis-amide)

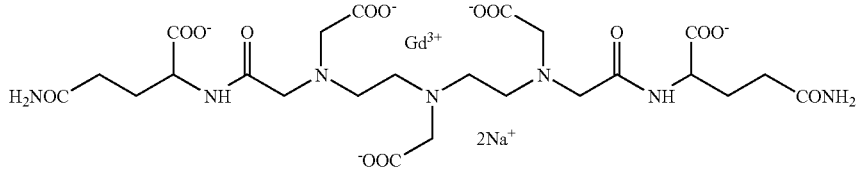

a) Preparation of 6,16-dicarbonyl-5,19-dicarboxy-5,8,11,14,17-pentaaza-8,11,14-tricarboxymethyl-heneicosandioic Acid Diamide A solution of L-glutamine (5.00 g; 0.0342 mol) in water (80 ml) is loaded into a 100-ml reaction flask and sodium hydroxide (1.37 g; 0.0342 mol) is added thereto. While keeping the reaction temperature at 15-20° C., diethylenetriaminopentaacetic acid bis-anhydride obtained as described in step a) of Example 1 (6.11 g; 0.0171 mol) is added portionwise and the reaction mixture is stirred under nitrogen atmosphere for 4 hours. The pH of the reaction mixture is then neutralised by the addition of HCl and the solvent is evaporated off under reduced pressure yielding a white product that is purified by column chromatography on Amberlite™ XAD 1180 at pH 2 eluting with water.

The $^1$H-NMR, 13C-NMR, IR and MS spectra are consistent with the indicated structure.

b) Preparation of the Gadolinium Complex of 6,16-dicarbonyl-5,19-dicarboxy-5,8,11,14,17-pentaaza-8,11,14-tricarboxymethyl-heneicosandioic Acid Diamide The gadolinium complex of the chelating ligand of step b) above has been prepared by following the same general procedure described in step c) of Example 1.

Example 3

Preparation of the Gadolinium Complex of 3,6,9-triaza-3,6,9-tricarboxymethylundecanoic Acid bis-glucopyranosylamide

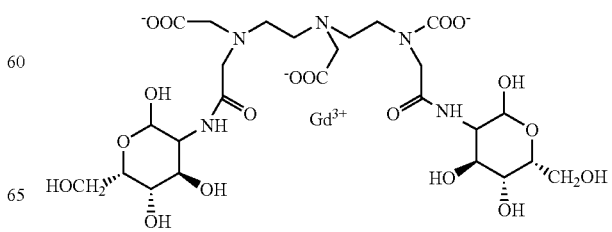

(gadolinium complex of N,N'-glucosamin-diethylenetriaminopentaacetic Acid bis-amide)

a) Preparation of 3,6,9-triaza-3,6,9-tricarboxymethylundecanoic Acid bis-glucopyranosylamide A solution of glucosamine (1.00 g; 0.00463 mol) in DMSO (10 ml) is charged into a 100-ml reaction flask and kept under stirring at 40° C. A solution of diethylenetriaminopentaacetic acid bis-anhydride obtained as described in step a) of Example 1 (0.746 g; 0.00209 mol) in DMSO (5 ml) is slowly added thereto and the reaction mixture is stirred under nitrogen atmosphere for 4 hours. Methanolic KOH is added to bring the pH of the reaction mixture to 8 and the reaction product is then precipitated by addition of methanol followed by the addition of acetone. The precipitate is washed several times with fresh acetone to remove DMSO still present and the product is then dried under vacuum. Yield 64%.

The $^1$H-NMR, 13C-NMR, IR and MS spectra are consistent with the indicated structure.

b) Preparation of the Gadolinium Complex of 3,6,9-triaza-3,6,9-tricarboxymethylundecanoic Acid bis-glucopyranosylamide The gadolinium complex of the chelating ligand of step b) above has been prepared by following the same general procedure described in step c) of Example 1.

Example 4

Preparation of the Gadolinium Complex of 2,24-diamino-8,18-dicarbonyl-7,10,13,16,19-pentaaza-10,13,16-tricarboxymethyl-pentaheicosandioic Acid (Gadolinium Complex of N,N'-(5-amino-5-carboxy-pentyl) diethylenetriaminopentaacetic Acid bis-amide)

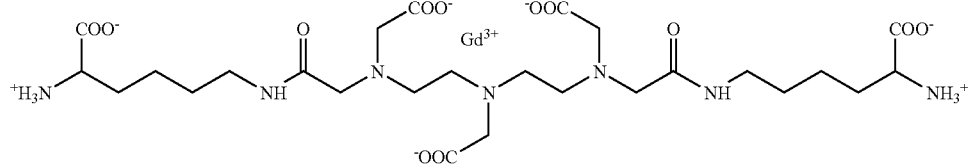

a) 2,24-diamino-8,18-dicarbonyl-7,10,13,16,19-pentaaza-10,13,16-tricarboxymethyl-pentaheicosandioic Acid N-tertbutoxycarbonyl-L-lysine (0.950 g; 0.00386 mol) and DMSO (10 ml) are charged into a 100-ml reaction flask and stirred at 50° C. until complete solution. A solution of diethylenetriaminopentaacetic acid bis-anhydride obtained as described in step a) of Example 1 (0.690 g; 0.00193 mol) in DMSO (5 ml) is slowly added thereto over a period of about one hour. After about 24 hours methanolic KOH is added to bring the pH of the reaction mixture to 8 and then acetone is added to precipitate the product which is then washed several times with fresh acetone. Upon removal of the solvent the obtained solid is dried at 40° C. in an oven yielding 1.05 g (64%) of the N,N'-tertbutoxycarbonyl derivative of the compound of the title. Deprotection to give the compound of the title is then achieved by stirring for 96 hours the solid in diethyl ether containing 1M HCl (6 ml). A pale yellow solid is thus obtained.

The $^1$H-NMR, 13C-NMR, IR and MS spectra are consistent with the indicated structure.

b) Preparation of the Gadolinium Complex of 2,24-diamino-8,18-dicarbonyl-7,10,13,16,19-pentaaza-10,13,16-tricarboxymethyl-pentaheicosandioic Acid The gadolinium complex of the chelating ligand of step b) above has been prepared by following the same general procedure described in step c) of Example 1.

Example 5

Preparation of the Gadolinium Complex of 2,16-dibenzyl-4,13-dicarbonyl-3,6,9,12,15-pentaaza-6,9,12-tricarboxymethyl-heptadecandioic Acid (Gadolinium Complex of N,N'-phenylalanyl-diethylenetriaminopentaacetic Acid bis-amide)

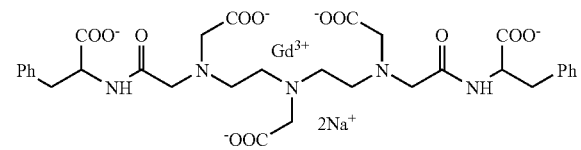

a) Preparation of 2,16-dibenzyl-4,13-dicarbonyl-3,6,9,12,15-pentaaza-6,9,12-tricarboxymethyl-heptadecandioic Acid A solution of phenyalanine (0.66 g; 0.002 mole) in DMSO (10 ml) is loaded into a 100-ml reaction flask and the mixture is heated to 50° C. under stirring. A solution of diethylenetriaminopentaacetic acid bis-anhydride obtained as described in step a) of Example 1 (0.715 g; 0.002 mol) in DMSO (6 ml) is slowly added thereto over a period of about two hour. The reaction mixture is allowed to react at 50° C. for 4 hours and at room temperature for additional 20 hours. At the end of this time the solution is clear but a lower yellow phase of a jelly consistency is present. The DMSO phase is recovered by decantation and acetone is added thereto until precipitation of a solid product is complete. The lower yellow phase is dissolved in a small amount of water and acetone is added thereto to get an additional crop of solid precipitate. The two crops are combined and washed several times under stirring with fresh acetone: The surnatant is then removed and the solid is taken up with water and washed again with fresh acetone. The raw material thus obtained is dissolved in acidic water (pH=2) and purified by column chromatography on Amberlite™ XAD 1180.

The $^1$H-NMR, 13C-NMR, IR and MS spectra are consistent with the indicated structure.

b) Preparation of the Gadolinium Complex of 2,16-dibenzyl-4,13-dicarbonyl-3,6,9,12,15-pentaaza-6,9,12-tricarboxymethyl-heptadecandioic Acid The gadolinium complex of the chelating ligand of step b) above has been prepared by following the same general procedure described in step c) of Example 1.

Example 6

Preparation of the Gadolinium complex of 10,20-dicarbonyl-4,9,12,15,18,21,26-heptaaza-12,15,18-tricarboxymethyl-nonaheicosan-1,29-diamine (Gadolinium Complex of N,N'-spermidin-diethylentriaminopentaneacetic Acid bis-amide)

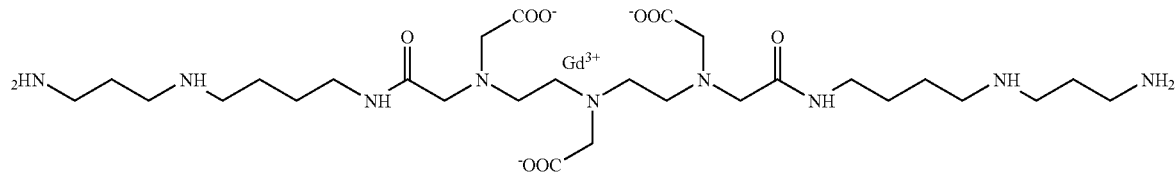

a) Preparation of 10,20-dicarbonyl-4,9,12,15,18,21,26-heptaaza-12,15,18-tricarboxy-methyl-nonaheicosan-1,29-diamine A solution of diethylenetriaminopentaacetic acid bis-anhydride obtained as described in step a) of Example 1 (0.357 g; 0.001 mol) in DMSO (5 ml) is added over a period of two hours to a solution of N-(3-aminopropyl)-1,4-butanediamine (spermidine, 1.45 g; 0.01 mol) in DMSO (20 ml) stirred at 50° C. in a 100-ml reaction flask. The reaction mixture is allowed to react at 50° C. for 4 hours and then at room temperature for additional 20 hours. At the end of this time the solution is clear but a lower yellow phase of a jelly consistency is present. The DMSO phase is recovered by decantation and acetone is added thereto until precipitation of a solid product is complete. The lower yellow phase is dissolved in a small amount of water and acetone is added thereto to get an additional crop of solid precipitate. The two crops are combined and washed several times under stirring with fresh acetone. The surnatant is then removed and the solid is taken up with water and washed again with fresh acetone. The raw material thus obtained is dissolved in acidic water (pH=2) and purified by column chromatography on Amberlite™ XAD 1180.

The $^1$H-NMR, 13C-NMR, IR and MS spectra are consistent with the indicated structure.

b) Preparation of the Gadolinium Complex of 10,20-dicarbonyl-4,9,12,15,18,21,26-heptaaza-12,15,18-tricarboxymethyl-nonaheicosan-1,29-diamine The gadolinium complex of the chelating ligand of step b) above has been prepared by following the same general procedure described in step c) of Example 1.

Example 7

Preparation of the Gadolinium Complex of 4,26-diamino-5,10,20,25-tetracarbonyl-12,15,18-tricarboxymethyl-6,9,12,15,18,21,24-heptaaza-nonaheicosan-1,29-diguanidina (Gadolinium complex of N,N'-arginylethylendiammino-diethylentraminopentaneacetic Acid bis-amide)

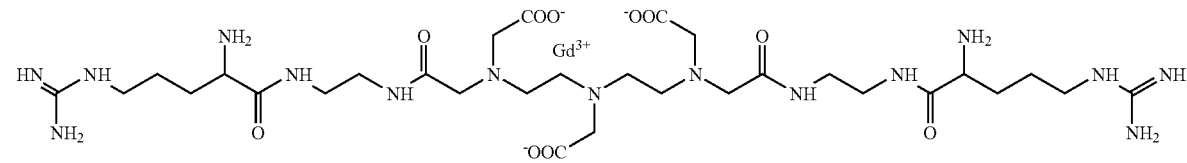

a) Preparation of 4,26-diamino-5,10,20,25-tetracarbonyl-12,15,18-tricarboxymethyl-6,9,12,15,18,21,24-heptaaza-nonaheicosan-1,29-diguanidina 2-amino-5-guanidino-valeric acid (arginine, 0.871 g; 0.005 mol) is dissolved in an aqueous solution at pH 9 and a strong excess of benzyl chloroformate is then slowly added thereto. The thus obtained corresponding tri-carbobenzyloxy derivative is isolated, dissolved in methylene chloride and added with di-cyclohexylcarbodiimide. The obtained solution is then slowly added to a solution of ethylenediamine (1.5 g; 0.025 mol) in methylene chloride. The 2-aminoethylamide of the tri-carbobenzyloxy protected arginine is recovered, dissolved in DMSO and a solution of diethylentriaminopentaneacetic acid bis-anhydride (1.78 g; 0.005 mol) in DMSO is then added to the obtained solution heated to 50° C. The reaction mixture is stirred at this temperature for 4 hours and then cooled to room temperature. The pH is adjusted to 8 by the addition of methanolic KOH and the raw product that precipitates is washed with acetone under stirring overnight. The solid is then recovered, dissolved in methanol and the protecting carbobenzyloxy groups are removed by catalytic hydrogenation over Pd/C 5%. Any residual carbamic acid that may possibly be present is then removed by acidification with HCl yielding the desired compound.

The $^1$H-NMR, 13C-NMR, IR and MS spectra are consistent with the indicated structure.

b) Preparation of the Gadolinium Complex of 4,26-diamino-5,10,20,25-tetracarbonyl-12,15,18-tricarboxymethyl-6,9,12,15,18,21,24-heptaaza-nonaheicosan-1,29-diguanidina The gadolinium complex of the chelating ligand of step b) above has been prepared by following the same general procedure described in step c) of Example 1.

Example 8

Preparation of [[N,N-Bis[2-[bis(carboxymethyl)amino]ethyl]-L-γ-glutamyl-L-glutaminato(6-)]gadolinate(3-)] Trisodium Salt (Gadolinium Complex of N,N-Bis[2-[bis(carboxymethyl)amino]ethyl]-L-γ-glutaminyl-L-glutamine)

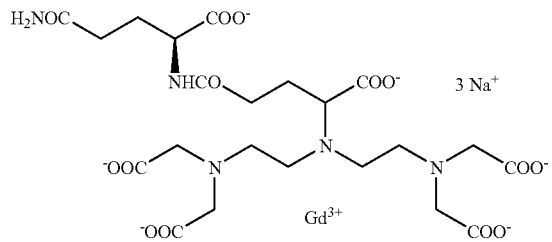

a) Preparation of N,N-Bis[2-[bis(1,1-dimethylethoxy)-2-oxoethyl]amino]ethyl]-L-γ-glutamyl-L-glutamine bis(1,1-dimethylethyl) Ester A solution of N-(3-dimethylaminopropyl)-N'-ethylcarbodiimide hydrochloride (EDCI) (1.93 g; 10.00 mmol) in $CH_2Cl_2$ was added over 20 min to a solution of N,N-bis[2-[bis(1,1-dimethylethoxy)-2-oxoethyl]amino]ethyl]-L-glutamic acid 1-(1,1-dimethylethyl) ester (6.25 g; 8.38 mmol) (i) and N-hydroxysuccinimide (NHS) (1.16 g; 10.05 mmol) in $CH_2Cl_2$ stirred at 0-5° C. After 24 h at room temperature the reaction solution was washed with $H_2O$, dried ($Na_2SO_4$) and evaporated to give the activated ester which was dissolved in $CH_2Cl_2$. This solution was added dropwise over 30 min to a solution of L-glutamine (1,1-dimethylethyl) ester hydrochloride (2 g; 8.38 mmol) (ii) and triethylamine (1.27 g; 12.55 mmol) in $CH_2Cl_2$ at room temperature. After 3 days at room temperature the solution was washed with $H_2O$ and dried ($Na_2SO_4$). The solution was evaporated to give a crude (7.77 g) that was purified by flash-chromatography (iii) to give 3.94 g (4.24 mmol) as a pale yellow oil. Yield 51%.

The $^1$H-NMR, 13C-NMR, IR and MS spectra are consistent with the indicated structure.

b) Preparation of N,N-Bis[2-[bis(carboxymethyl)amino]ethyl]-L-γ-glutamyl-L-glutamine Trifluoroacetic acid (12.4 mL; 162.3 mmol) was added to a solution of the compound obtained in the step a) (5.03 g; 5.4 mmol) in $CH_2Cl_2$ (100 mL) and stirred at room temperature for 48 h. The solvent was evaporated and the residue was dissolved in trifluoroacetic acid (10 mL). After 48 h at room temperature the acid was evaporated and the crude was treated with $Et_2O$, then filtered. The solid was suspended twice in $Et_2O$ and filtered to give a white solid (3.76 g, 4.1 mmol). Yield 75%.

The $^1$H-NMR, 13C-NMR, IR and MS spectra are consistent with the indicated structure.

c) Preparation of [[N,N-Bis[2-[bis(carboxymethyl)amino]ethyl]-L-γ-glutamyl-L-glutaminato(6-)]Gadolinate(3-)] Trisodium Salt A solution of the compound obtained in the step b) (2.77 g; 3.00 mmol) in $H_2O$ was adjusted to pH 7.7 by addition of 2 N NaOH (5 mL); $Gd_2O_3$ (1.03 g; 2.80 mmol) was added and the suspension was stirred at 50° C. for 24 h. As the pH was 12, 1 N HCl (2 mL) was added to reach the value of 7. The excess $Gd_2O_3$ was filtered off (0.43 g; 1.20 mmol) and the solvent was evaporated to give the product as a pale yellow solid (3.10 g; 2.95 mmol). Yield 98%.

Example 9

Preparation of [[N,N-Bis[2-[bis(carboxymethyl)amino]ethyl]-L-γ-glutamyl(5-)-agmatine]gadolinate(3-)]disodium Salt (Gadolinium Complex of N,N-Bis[2-[bis(carboxymethyl)amino]ethyl]-L-γ-glutamyl-agmatine)

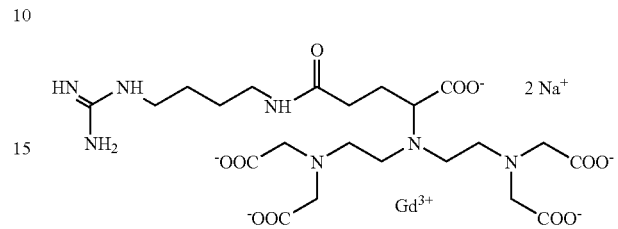

a) Preparation of N,N-Bis[2-[bis(1,1-dimethylethoxy)-2-oxoethyl]amino]ethyl]-L-γ-glutamyl-agmatine N-hydroxysuccinimide (1.41 g; 12.29 mmol) was added to a solution of N,N-bis[2-[bis(1,1-dimethylethoxy)-2-oxoethyl]amino]ethyl]-L-glutamic acid 1-(1,1-dimethylethyl) ester (7.64 g; 10.24 mmol) in $CH_2Cl_2$ (100 mL). The mixture was cooled at 0° C. and a solution of EDCI (2.36 g; 12.29 mmol) in $CH_2Cl_2$ (45 mL) was added dropwise. The mixture was stirred at room temperature, monitoring the reaction by TLC. When the starting material was completely consumed, the solution was washed with water (3×100 mL), dried ($Na_2SO_4$) and evaporated. The residue (9.28 g) was dissolved in DMF (120 mL) and agmatine (1.19 g, 10.24 mmol) was suspended in the solution. The mixture was stirred at room temperature for 2 d. The solution was filtered and water (150 mL) was added. The solution was washed with $Et_2O$ and the evaporated organic phase was treated with brine (100 mL). The aqueous phase was extracted with $Et_2O$ and organic phase was dried and evaporated. The residue was purified by flash chromatography to give the compound (1.71 g; 1.99 mmol) as yellow non-crystalline solid. Yield 19%

The $^1$H-NMR, 13C-NMR, IR and MS spectra are consistent with the indicated structure.

b) Preparation of N,N-Bis[2-[bis(carboxymethyl)amino]ethyl]-L-γ-glutamyl-agmatine The compound obtained ad indicated in step a) (1.48 g; 1.72 mmol) was dissolved in $CH_2Cl_2$ (15 mL) and TFA (3.3 mL; 43 mmol) was added to the solution. The mixture was stirred at room temperature. After 4 days the solvent was removed under reduce pressure to give 1.56 g of crude product. The raw materials was dissolved in pure TFA (5 mL) and the mixture was stirred at room temperature overnight. TFA was removed under reduced pressure and the residue was crystallized with $Et_2O$ and filtered to give a white crystalline solid. Because of the presence of $Et_2O$ and TFA in the final product, the solid was dissolved in water again and evaporated under reduce pressure for three times. The final product was obtained as white crystalline solid (0.77 g; 1.33 mmol). Yield: 97%.

The $^1$H-NMR, 13C-NMR, IR and MS spectra are consistent with the indicated structure.

c) Preparation of [[N,N-Bis[2-[bis(carboxymethyl)amino]ethyl]-L-γ-glutamyl(5-)-agmatine]gadolinate (3-)]disodium Salt The compound as obtained in the previous step b) was dissolved in 10 mL of water and NaOH 1M was added (2.3 mL). Then NaOH 0.1M was slowly added until the pH of final solution was 7. $Gd_2O_3$ (210 mg; 0.58 mmol) was suspended and the mixture was heated at 50° C. overnight. Because of pH of the solution raised to 11.8, HCl 1M (0.6 mL) was added to adjust the pH to 5. The mixture was maintained at room temperature for further 48 h then filtered (Millipore HA 0.45) to eliminate the unreacted $Gd_2O_3$. The pH of the solution was adjusted to 6.4 and the solvent was evaporated under reduced pressure to give 0.95 g (1.22 mmol) of white crystalline solid.

Example 10

Preparation of [[N,N-Bis[2-[bis(carboxymethyl) amino]ethyl]-L-γ-glutamyl(5-)-arginine]gadolinate (3-)]disodium Salt (Gadolinium Complex of N,N-Bis[2-[bis(carboxymethyl) amino]ethyl]-L-γ-glutamyl-arginine)

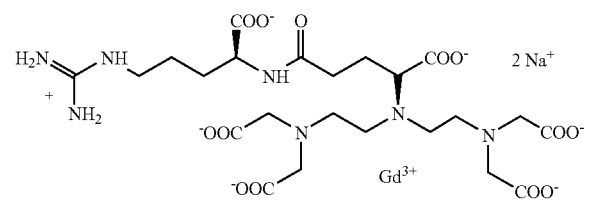

a) Preparation of N,N-bis[2-[bis(1,1-dimethylethoxy)-2-oxoethyl]amino]ethyl]-L-γ-glutamyl[2-amino-5-[N'[(2,3,6-trimethyl-4-methoxy)benzensulfonyl]]guanidine-1-(1,1-dimethylethyl)ester]-L-glutamic Acid 1-(1,1-dimethylethyl) Ester

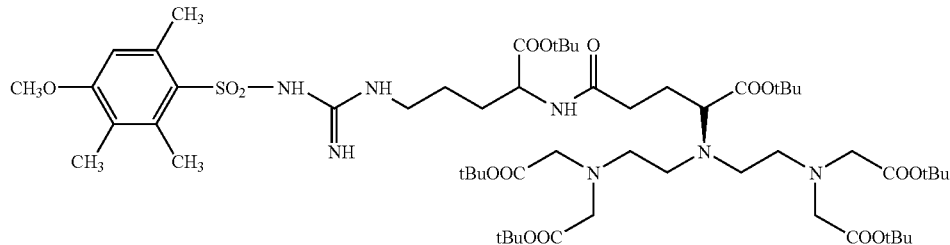

N-hydroxysuccinimide (773 mg; 6.72 mmol) was added to a solution of N,N-bis[2-[bis(1,1-dimethylethoxy)-2-oxoethyl]amino]ethyl]-L-glutamic acid 1-(1,1-dimethylethyl) ester (4.18 g; 5.6 mmol) in $CH_2Cl_2$ (55 mL). The mixture was cooled at 0° C. and a solution of EDCI (1.29 g; 6.72 mmol) in $CH_2Cl_2$ (25 mL) was added dropwise. The mixture was stirred at room temperature, monitoring the reaction by TLC. When the starting material was completely consumed, the solution was washed with water (3×60 mL), dried ($Na_2SO_4$) and evaporated. The residue (4.81 g) was dissolved in $CH_2Cl_2$ (55 mL) and 2-amino-5-[N'[(2,3,6-trimethyl-4-methoxy) benzensulfonyl]]guanidine-1-(1,1-dimethylethyl)ester (2.5 g; 5.6 mmol) was added to the solution. The mixture was stirred at room temperature for 25 h. The solution was washed with water (3×50 mL) and the organic phase was dried and evaporated. The residue was purified by flash chromatography to give the product (5.45 g; 4.66 mmol) as white crystalline solid. Yield 83%

The $^1$H-NMR, 13C-NMR, IR and MS spectra are consistent with the indicated structure.

b) Preparation of N,N-Bis[2-[bis(carboxymethyl)amino] ethyl]-L-γ-glutamyl-arginine The compound obtained in step a) (2.5 g; 2.14 mmol) was dissolved in a mixture of TFA (63 mL) and thioanisole (7 mL). The solution was stirred at room temperature. After 2 days the solvent was removed under reduce pressure and the residue was dissolved in HCl 1 N (18 mL) and evaporated; this procedure was repeated three times. The residue was dissolved in water and extracted with $CHCl_3$. The aqueous solution was evaporated to obtained a crude (1.79 g) that was dissolved in water (6 mL), adjusted to pH 1.7 by addition of NaOH 1M and purified by percolation through Amberlite XAD 1600T resin column to give the product (1.03 g; 1.66 mmol) as white crystalline solid. Yield: 78% c) Preparation of [[N,N-Bis[2-[bis(carboxymethyl)amino] ethyl]-L-γ-glutamyl(5-)-arginine]gadolinate (3-)]disodium Salt The compound as obtained in the step b) was dissolved in water (15 mL) and NaOH 1M was added (2.5 mL) until the pH of the solution was 3.9 (0.5 mL). $Gd_2O_3$ (217 mg; 0.6 mmol) was added and the solution was heated to 50° C. overnight. Because of pH of the solution raised to 12.5, HCl 1M (0.35 mL) was added to adjust the pH to 6.5. The mixture was maintained at room temperature for further 3 days, then it was filtered (Millipore HA 0.45 filter) to eliminate the unreacted $Gd_2O_3$. The pH was adjusted to 6.90 and the solvent was evaporated under reduced pressure to give 1.08 g (1.32 mmol) of white crystalline solid.

Example 11

Preparation of Gadolinium Complex of [4-(1,6,10-triazaundecan)-phenyl-aminocarbonylmethyl]-1,4,7, 10-tetraazacyclododecan-4,7,10-triacetic Acid

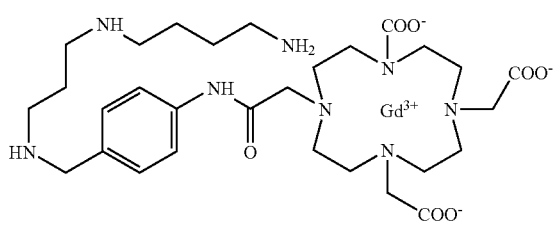

a) Preparation of 3-[(4-Aminobutyl)amino]propanenitrile

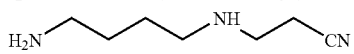

Acrylonitrile (5.08 g, 0.096 mol) was added to ice bath-cooled 1,4-butanediamine (8.44 g, 0.096 mol) in 30 min. The resulting mixture was stirred for 2 h at RT, heated to 50° C. for further 3 h and finally let stirring at RT overnight. After Kugelrohr distillation a colourless oil was obtained (5.80 g, 0.041 mol yield 42.8%).

The $^1$H-NMR, 13C-NMR, IR and MS spectra are consistent with the indicated structure.

b) Preparation of Tert-Butyl N-{4-{[(tert-Butyloxy)carbonyl]amino}butyl}-N-(2-cyanoethyl) Carbamate

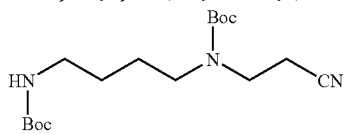

BOC-ON (9.41 g, 0.038 mol) and was added in small portions to a solution of 3-[(4-Aminobutyl)amino]propanenitrile (2.70 g, 0.019 mol) and triethylamine (6.00 g, 0.059 mol) in dioxane/H$_2$O (9:1 v/v, 50 cm$^3$). The resulting mixture was stirred at room temperature for 3 days; then the solvent was removed under reduced pressure. The resulting pale yellow oil was dissolved in Et$_2$O (80 cm$^3$) and washed with 1M NaOH (3×30 cm$^3$) and brine (2×25 cm$^3$). The organic fraction was dried over Na$_2$SO$_4$ and filtered. After removal of the solvent, a pale yellow oil was obtained which was dried under reduced pressure (6.041 g, 0.0177 mol, yield 92.7%).

The $^1$H-NMR, 13C-NMR, IR and MS spectra are consistent with the indicated structure.

c) Preparation of Tert-Butyl N-(3-aminopropyl)-N-{4-{[(tert-Butyloxy)carbonyl]amino}butyl}carbamate.

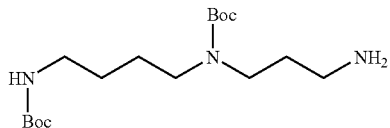

The product as obtained in step b) (2.07 g, 6.066 mmol) and NaOH (0.6 g, 0.015 mol) were dissolved in 94% EtOH (30 ml). After addition of Ni-Raney as catalyst, the resulting mixture was hydrogenated under pressure (10 bar). After filtration through celite, the solvent volume was reduced to 5 cm$^3$ and the product was extracted with CHCl$_3$ (5×50 cm$^3$.) The collected organic fractions were dried over Na$_2$SO$_4$ and filtered. After removal of the solvent, a pale yellow oil was obtained which was dried under reduced pressure (1.826 g, 5.29 mmol, yield 87.2%).

The $^1$H-NMR, 13C-NMR, IR and MS spectra are consistent with the indicated structure.

d) Preparation of 1,6-bis-(tert-Butyloxycarbonyl)-11-p-nitrophenyl-1,6,10-triazaundecane.

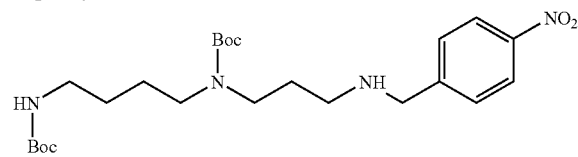

To a solution of the compound as obtained in step c) (1.64 g, 4.30 mmol) in Et$_2$O (30 cm$^3$) 4-nitrobenzaldehyde (0.716 g, 4.30 mmol) dissolved in a mixture of Et$_2$O and THF (20 cm$^3$, 1:1 v/v) was added in 1 h. The resulting mixture was stirred at RT for 24 h and then the solvent was removed at the rotary evaporator. The reddish oil obtained was dissolved in EtOH (30 cm$^3$) and NaBH$_4$ (0.488 g, 12.9 mmol) was added in small portions. The resulting solution was stirred at RT for 5 h. After removal of the solvent the product was recovered with H$_2$O, basified with 1M NaOH and extracted with CH$_2$Cl$_2$ (5×50 cm$^3$). The collected organic fractions were dried over Na$_2$SO$_4$ and filtered to yield a yellow oil which was purified by column chromatography (from EtOAc 100% to EtOAc/MeOH 95:5) (0.550 g, 1.146 mmol, yield 26.6%).

The $^1$H-NMR, 13C-NMR, IR and MS spectra are consistent with the indicated structure.

e) Preparation of 1,6-bis-(tert-Butyloxycarbonyl)-11-p-aminophenyl-1,6,10-triazaundecane

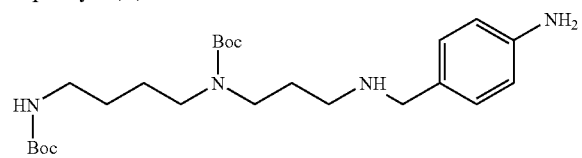

A mixture of the compound obtained in step d) (0.183 g, 0.382 mmol) in EtOH (20 cm$^3$) and of FeO(OH) as catalyst (20 mg) was heated to 60° C. under N$_2$ atmosphere. Then hydrazine hydrate (19.5 mg, 0.60 mmol) was added and the resulting mixture was stirred 18 h at RT. After filtration through celite the solvent was removed at the rotary evaporator to yield a yellow oil which was dried under reduced pressure. (0.112 g, 0.248 mmol, yield 65.0%).

The $^1$H-NMR, 13C-NMR, IR and MS spectra are consistent with the indicated structure.

f) Preparation of 1,6-bis-(tert-Butyloxycarbonyl)-11-(4-bromoacetamidophenyl)-1,6,10-triazaundecane.

To a suspension of K$_2$CO$_3$ (304.0 mg, 2.2 mmol) and of the product obtained in the previous step e) (100.0 mg, 0.22 mmol) in dry CH$_3$CN (15 cm$^3$) cooled to 0° C. and kept under N$_2$ atmosphere, a solution of Bromoacetyl bromide (42.4 mg, 0.22 mmol) in dry CH$_3$CN (10 cm$^3$) was added in 1 h. After 3 h the mixture was filtered and the solvent was removed at the rotary evaporator to yield a yellow oil which was dried under reduced pressure (99.4 mg, 0.174 mmol, yield 79.0%).

The $^1$H-NMR, 13C-NMR, IR and MS spectra are consistent with the indicated structure.

g) Preparation of [4-(1,6-bis-(tert-Butyloxycarbonyl)-1,6,10-triazaundecan)-phenyl-aminocarbonylmethyl]-1,4,7,10-tetraazacyclododecan-4,7,10-triacetic Acid tris-tert-butylester.

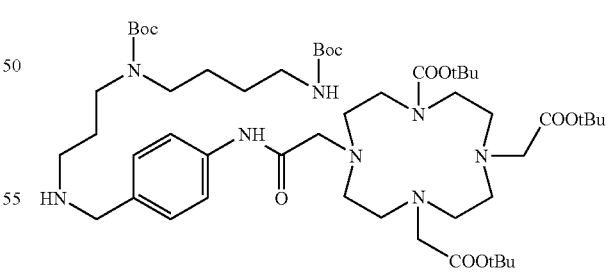

To a suspension of K$_2$CO$_3$ (215.0 mg, 2.2 mmol) and of DO3AtBu (103.6 mg, 0.174 mmol) in dry CH$_3$CN (15 cm$^3$) heated to 80° C. and kept under N$_2$ atmosphere, a solution of the compound obtained in step f) (99.4 mg, 0.174 mmol) in dry CH$_3$CN (10 cm$^3$) was added in 1 h After 18 h the mixture was filtered and the solvent was removed at the rotary evaporator to yield a brown oil which was dried under reduced pressure (100.4 mg, 0.10 mmol, yield 57.4%).

The ¹H-NMR, 13C-NMR, IR and MS spectra are consistent with the indicated structure.

h) Preparation of [4-(1,6,10-triazaundecan)-phenyl-aminocarbonylmethyl]-1,4,7,10-tetraazacyclododecan-4,7,10-triacetic Acid.

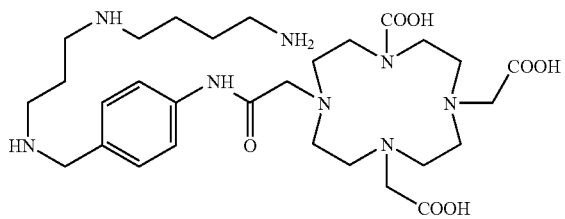

The compound obtained in step g) (100.4 mg, 0.10 mmol) was dissolved in a mixture $CH_2Cl_2$/TFA (1:1, v/v, 20 cm³) and stirred at RT for 4 h after which a reddish oil was formed. After decantation of the solution, MeOH (10 cm³) was added and a yellow solid was formed. The solid was then collected and dried under reduced pressure (45.4 mg, 0.071 mmol, yield 71.3%).

The ¹H-NMR, 13C-NMR, IR and MS spectra are consistent with the indicated structure.

i) Preparation of the Gadolinium Complex of [4-(1,6,10-triazaundecan)-phenyl-aminocarbonylmethyl]-1,4,7,10-tetraazacyclododecan-4,7,10-triacetic Acid The gadolinium complex of the chelating ligand of step h) above has been prepared by following the same general procedure described in step c) of Example 1.

The possibility of using the compounds of the present invention to distinguish tumor cells from normal healthy cells, thus allowing the use of the contrast agents based thereon in the diagnosis of tumors, has been confirmed by evaluating the significantly increased rate of internalization of representative MRI detectable species (I) in various cells lines including tumor cells and comparatively normal healthy cells.

The experiments done and the results obtained are summarised hereinbelow.

Example 12

Analysis of the differential uptake of the compound of Example 1 in rat hepatocytes and human hepatoma cells HepG2, has been carried out as follows:

Rat hepatocytes were cultured in M199 medium supplemented with 2 mg/ml bovine serum albumin (BSA), 3.6 mg/ml Hepes, 100 U/ml penicillin, 100 U/µg streptomycin, and 10 nmol/l insulin; HEPG2 cells were cultured in RPMI 1640 medium supplemented with 10% foetal bovine serum, 100 U/ml penicillin and 100 U/µg streptomycin.

The uptake experiments were performed in 5 ml EBSS, Earl's Balanced Salt Solution, ($CaCl_2$ 0.266 g/l; KCl 0.4 g/l; NaCl 6.8 g/l; glucose 1 g/l; $MgSO_4$ 0.204 g/l; $NaH_2PO_4$ 0.144 g/l; $NaHCO_3$ 2.2 g/l).

Determination of Gd moles internalized was performed with the measure of relaxation rate at 20 MHz of cytosolic extracts after mineralization overnight at 120° C. in 37% HCl (1:1). The value has been normalised on 1 mg protein of the lisate of cells.

A time course analysis was done where cells were incubated at 37° C. in EBSS and then collected at different times (15', 30', 1 h, 2 h, 6 h).

The substrate concentration was for both cell lines 0.8 mM.

The results obtained show that after 1 hour the uptake of the compound of Example 1 by the human hepatoma cells HepG2 is 3 times more that the one in hepatocytes, and at 2 hours is more than 4 times higher, reaching a plateau after about two hours and a half. These results are graphically reported in FIG. 1.

Example 13

Differential uptake of the compound of Example 3 in hepatocytes and hepatoma cell lines HepG2.

The cells were cultured as in Example 12 above. The uptake experiments were performed in 5 ml EBSS without glucose to avoid competition between this compound and the test compound.

Determination of Gd moles internalized was performed with the measure of relaxation rate at 20 MHz of cytosolic extracts after mineralization at 120° C. in 37% HCl (1:1). The value was normalised on 1 mg protein of the lisate of cells.

The substrate concentration was 5.1 mM and a time course analysis was done.

Figure 2:
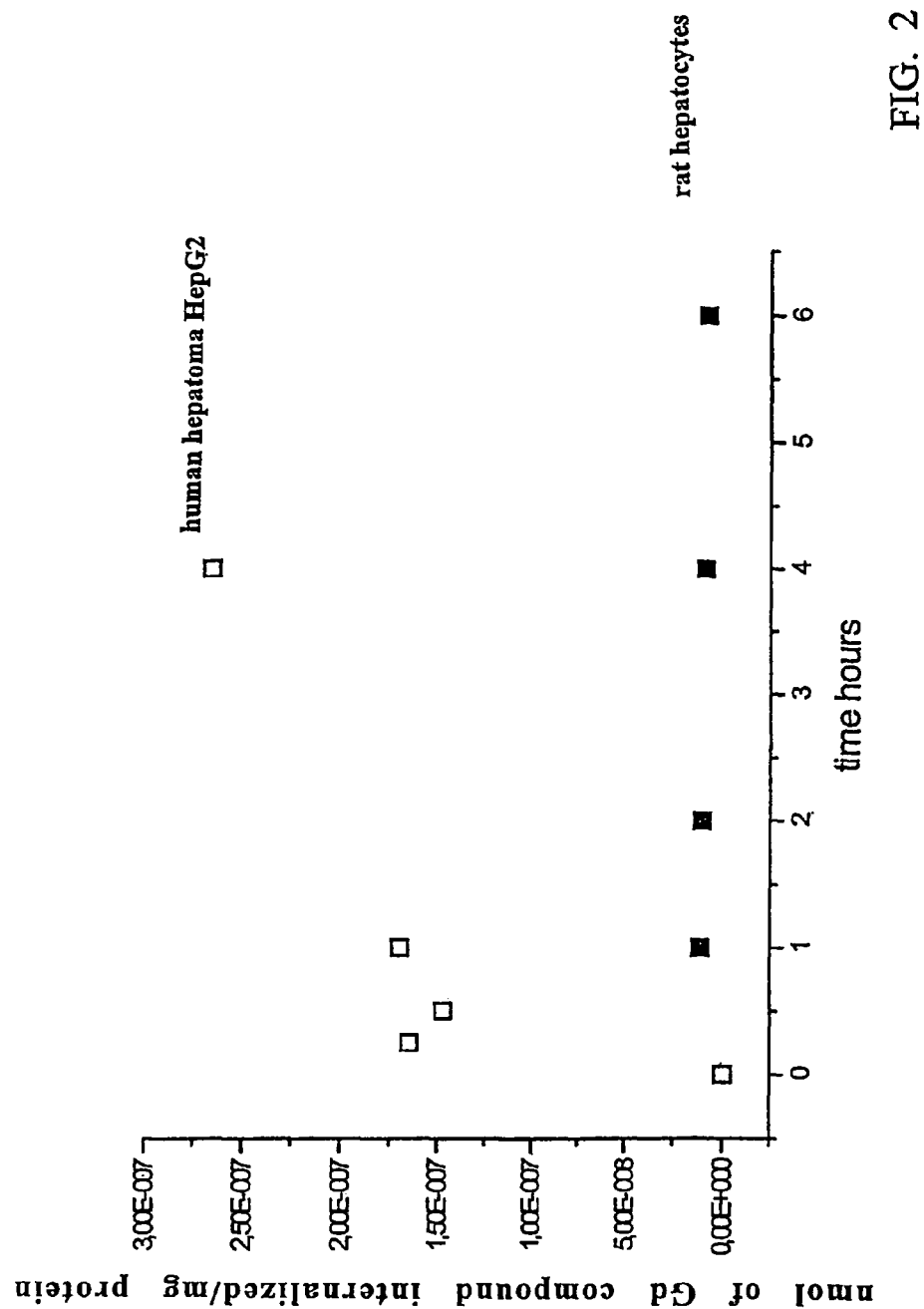

The results that show the higher uptake of the compound of Example 3 in human hepatoma cells HepG2 compared with hepatocyte are reported in FIG. 2.

Example 14

The uptake of the compound of Example 3 in a panel of cancer cell lines compared with healthy hepatocytes was evaluated by culturing the various cancer cell lines and performing the uptake experiments as described above.

Determination of the Gd moles internalized was performed with the measure of relaxation rate at 20 MHz of cytosolic extracts after mineralization at 120° C. in 37% HCl (1:1). The value was normalised on 1 mg protein of the lisate of cells.

The substrate concentration was 5.1 mM and the uptake was measured after 2 hours from the administration of the test compound.

Figure 3:
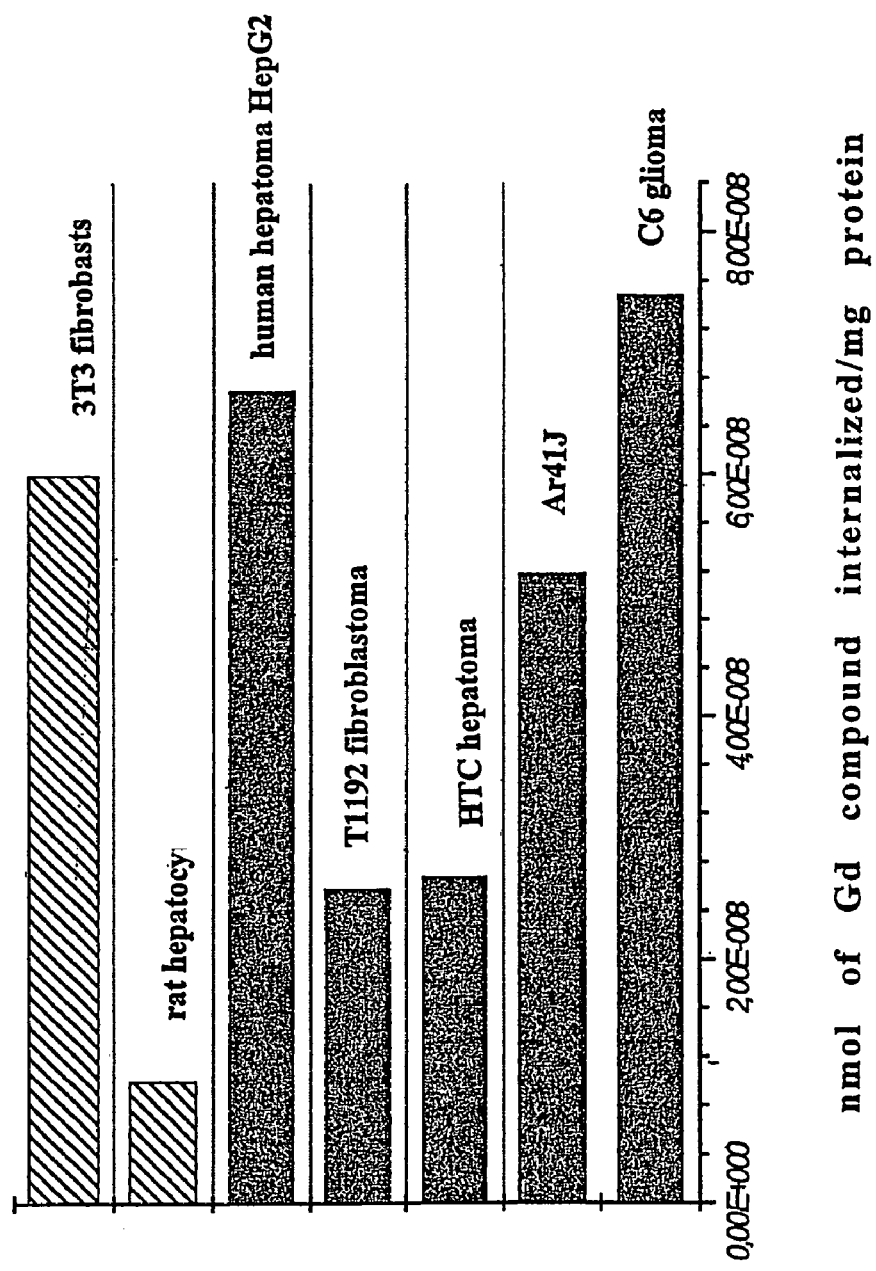

The uptake of Gd was increased in all the cancer cell lines with a value that is cell line dependent. These results are summarised in the histogram of FIG. 3.

Example 15

Analysis of the differential uptake of the compound of Example 8 in rat hepatocytes and human hepatoma cells HTC.

This experiment has been carried out as follows:

Rat hepatocytes were cultured in M199 medium supplemented with 2 mg/ml bovine serum albumin (BSA), 3.6 mg/ml Hepes, 100 U/ml penicillin, 100 U/µg streptomycin, and 10 nmol/l insulin; HTC cells were cultured in RPMI 1640 medium supplemented with 10% foetal bovine serum, 100 U/ml penicillin and 100 U/µg streptomycin.

The uptake experiments were performed in 5 ml EBSS, Earl's Balanced Salt Solution, ($CaCl_2$ 0.266 g/l; KCl 0.4 g/l; NaCl 6.8 g/l; glucose 1 g/l; $MgSO_4$ 0.204 g/l; $NaH_2PO_4$ 0.144 g/l; $NaHCO_3$ 2.2 g/l).

Determination of Gd moles internalized was performed with the measure of relaxation rate at 20 MHz of cytosolic extracts after mineralization overnight at 120° C. in 37% HCl (1:1). The value has been normalised on 1 mg protein of the lisate of cells.

Figure 4:
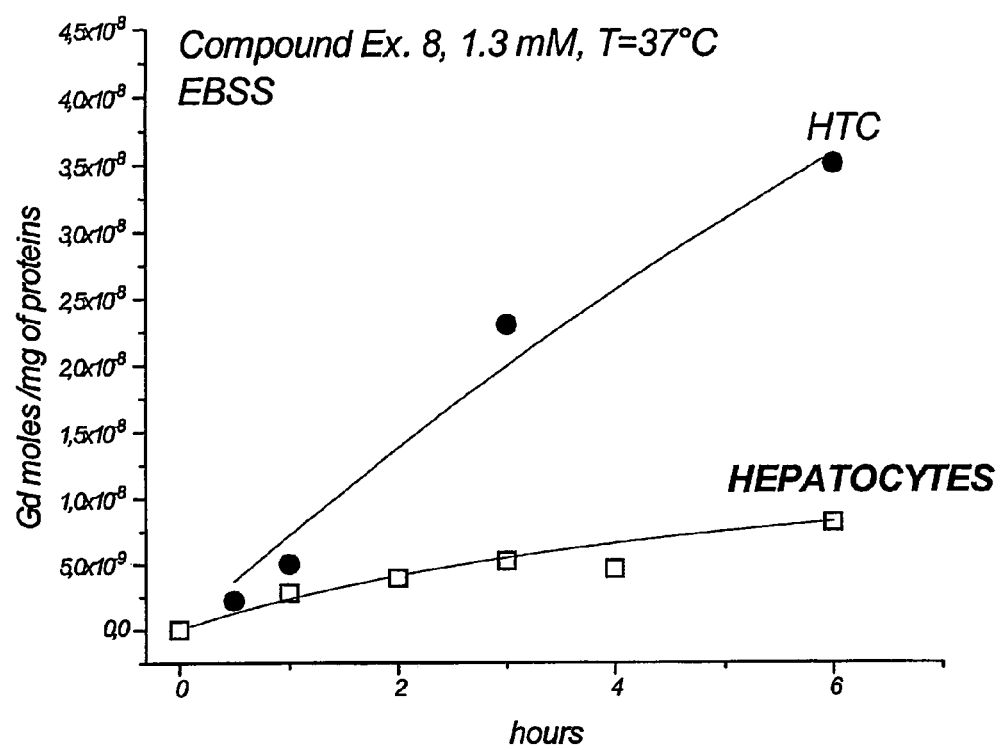
FIG. 4 reports the differential uptake of the compound of Example 8 by rat hepatocytes with respect to human hepatoma cells HTC.

A time course analysis was done where cells were incubated at 37° C. in EBSS and then collected at different times (1 h, 3 h, 6 h). The substrate concentration was for both cell lines 1.3 mM. The results obtained show that after 0.5 hour the uptake of the compound of Example 11 by the human hepatoma cells HTC is ⅓ times more that the one in hepatocytes, and at 2 hours is more than 3 times higher, reaching a value of more than 4 times higher after six hours. These results are graphically reported in FIG. 4.

Example 16

The uptake of the compound of Example 8 in a panel of cancer cell lines compared with healthy hepatocytes and 3T3 cell was evaluated by culturing the various cancer cell lines and performing the uptake experiments as described above.

Determination of the Gd moles internalized was performed with the measure of relaxation rate at 20 MHz of cytosolic extracts after mineralization at 120° C. in 37% HCl (1:1). The value was normalised on 1 mg protein of the lisate of cells.

The substrate concentration was 1.6 mM and the uptake was measured after 6 hours from the administration of the test compound.

Figure 5:
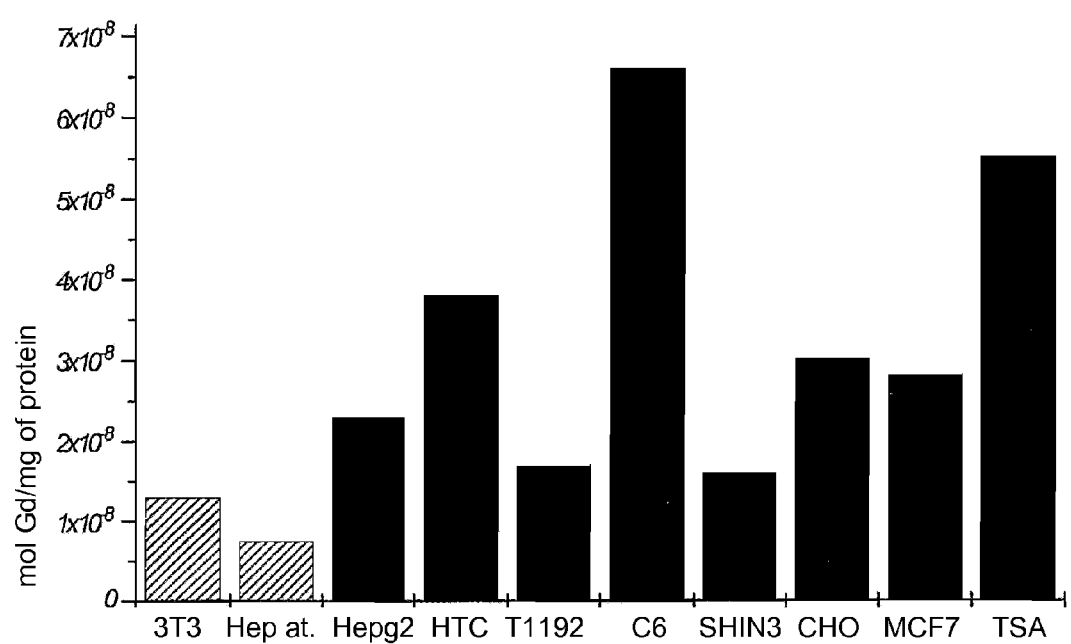
FIG. 5 reports the differential uptake of the compound of Example 8 in a panel of cancer cell lines with respect to healthy hepatocytes and 3T3 cells.

The uptake of Gd was increased in all the cancer cell lines with a value that is cell line dependent. These results are summarised in the histogram of FIG. 5.

Example 17

The uptake of the compound of example 8 in HTC cells as a function of the concentration of glutamine in the inoculation medium was evaluated by culturing the cancer cell lines and performing the uptake experiments as described above.

Determination of the Gd moles internalized was performed with the measure of relaxation rate at 20 MHz of cytosolic extracts after mineralization at 120° C. in 37% HCl (1:1). The value was normalised on 1 mg protein of the lisate of cells.

Figure 6:
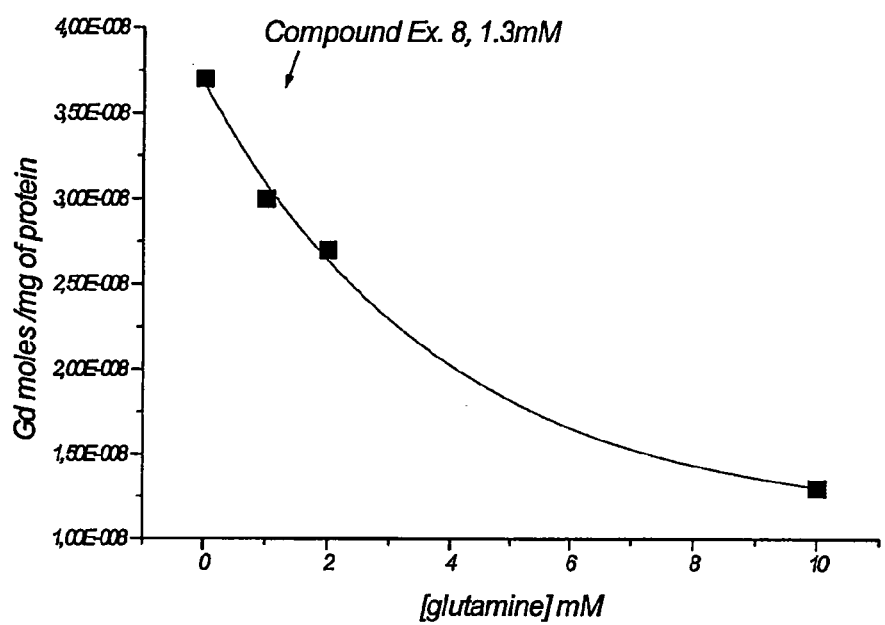
FIG. 6 reports the differential uptake of the compound of Example 8 in HTC cells as function of the concentration of glutamine.

The substrate concentration was 1.3 mM and the uptake was measured after 1, 2 and 10 hours from the administration of the test compound. Cells were incubated at 37° C. for 6 hours with a fixed amount of compound of example 8 and increasing concentration of the competitor glutamine (from 0.5 to 10 mM). These results are summarised in the histogram of FIG. 6.

It is worth to recall that a general indication to access the involvement of a given transporter in the internalization of a given I-structure can be drawn by a competitive assay with the nutrient or pseudo-nutrient of choice.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

The invention claimed is:

1. A MRI detectable species according to formula (I) which upon contact with the cells or cell surfaces of a human or other animal is incorporated into or onto the animal's cells or cell surfaces and which provides contrast sufficient to clearly distinguish between normal, healthy cells and tumor cells, wherein;

$$D_p-S_n-N_m \quad (I)$$

D is a MRI detectable moiety selected from the group consisting of coated ferromagnetic particles, coated superparamagnetic particles and chelated complexes of paramagnetic metal ions;

S is a spacer;

N is a molecule of a nutrient or pseudo-nutrient selected from alanine, phenylalanine, arginine, putrescine, spermidine, spermine, asparagine, agmatine and glutamine and n is 0 or an integer of 1 to 5, m is an integer of 1 to 5 and p is an integer of 1 to 10, wherein when n is an integer, p=1, m≧1 and n≦m.

2. The MRI detectable species of claim 1 wherein D contains at least one site for attachment to the spacer S or the nutrient/pseudo-nutrient molecule N.

3. The MRI detectable species of claim 1, wherein the moiety D is a chelated complex of a paramagnetic metal ion selected from the ions of transition and lanthanide metals with a chelating ligand L.

4. The MRI detectable species of claim 3, wherein the paramagnetic metal ion is selected from the ions having atomic number of 21 to 29, 42, 43, 44, or 57 to 71, and the chelating ligand L is selected from the group consisting of the residue of a polyaminopolycarboxylic acid, either linear or cyclic, in racemic or optically active form, selected from the group consisting of ethylenediaminotetracetic acid (EDTA), diethylenetriaminopentaacetic acid (DTPA), N-[2-[bis(carboxymethyl)-amino]-3-(4-ethoxyphenyl)propyl]-N-[2-[bis(carboxymethyl)amino]ethyl]-L-glycine (EOB-DTPA), N,N-bis[2-[bis(carboxymethyl)amino]ethyl]-L-glutamic acid (DTPA-GLU), N,N-Bis[2-[bis(carboxymethyl)amino]ethyl]-L-γ-glutamyl-L-glutamine, N,N-bis[2-[bis(carboxymethyl)amino]ethyl]-L-lysine (DTPA-LYS), the DTPA mono- or bis-amide derivatives, such as N,N-bis[2-[carboxymethyl[(methylcarbamoyl)-methyl]amino]ethyl] glycine (DTPA-BMA), 4-carboxy-5,8,11-tris(carboxymethyl)-1-phenyl-2-oxa-5,8,11-triazatridecan-13-oic acid (BOPTA), 1,4,7,10-tetraazacyclo-dodecan-1,4,7,10-tetraacetic acid (DOTA), 1,4,7,10-tetraazacyclododecan-1,4,7-triacetic acid (DO3A), 10-(2-hydroxypropyl)-1,4,7,10-tetraazacyclododecan-1,4,7-triacetic acid (HPDO3A), 2-methyl-1,4,7,10-tetraazacyclododecan-1,4,7,10-tetraacetic acid (MCTA), (α,α', α'',α''')-tetramethyl-1,4,7,10-tetraazacyclododecan-1,4,7, 10-tetraacetic acid (DOTMA), 3,6,9,15-tetraazabicyclo[9.3.1]pentadeca-1(15),11,13-triene-3,6,9-triacetic acid (PCTA), [4-(1,6,10-triazaundecan)-phenyl-aminocarbonylmethyl]-1,4,7,10-tetraazacyclododecan-4,7,10-triacetic acid; a derivative thereof wherein one or more of the carboxylic groups are in the form of the corresponding salts, esters, or amides; and the residue of a corresponding compound wherein one or more of the carboxylic groups is replaced by a phosphonic and/or phosphinic group selected from the group consisting of 4-carboxy-5,11-bis(carboxy-methyl)-1-phenyl-12-[(phenylmethoxy)methyl]-8-(phosphonomethyl)-2-oxa-5,8,11-triazatridecan-13-oic acid, N,N'-[(phosphonomethylimino)di-2,1-ethanediyl]bis[N-(carboxymethyl)glycine], N,N'-[(phosphonomethylimino)di-2,1-ethanediyl]bis[N-(phosphonomethyl)glycine], N,N'-[(phosphinomethylimino)di-2,1-ethanediyl]bis[N-(carboxymethyl)glycine], 1,4,7,10-tetraazacyclododecane-1,4,7,10-tetrakis[methylen(methylphosphonic)]acid, and 1,4,7,10-tetraazacyclododecane-1,4,7,10-tetrakis[methylen (methylphosphinic)]acid.

5. The MRI detectable species of claim 3 wherein the complex is formed with a metal ion selected from the group consisting of Mn, Fe, Eu, Gd and Dy.

6. The MRI detectable species of claim 1 wherein the spacer S, if present, is a homo- or hetero-bifunctional linker where the two reactive moieties are separated by alkylidene, alkenylidene, alkynylidene, cycloalkylidene arylidene, or aralkylidene radical that is optionally substituted and is optionally interrupted by heteroatoms.

7. The MRI detectable species of claim 6, wherein the reactive moieties are separated by an aliphatic, straight or branched chain, that optionally is interrupted by —O—, —S—, —CO—, —NR—, —CS— groups or by aromatic rings, and optionally bear an —OR, —SR, —NRR₁, —COOR, —CONRR₁ wherein R and R₁ are hydrogen atoms.

8. A process for the preparation of the MRI detectable species of claim 1, said process comprising:
   either conjugating the spacer, S, if present, with the nutrient or pseudo-nutrient molecule N and combining the obtained conjugate product and the MRI detectable moiety D; or
   conjugating the MRI detectable moiety D with the spacer S, if present, and combining the obtained conjugated product with the nutrient or pseudo-nutrient molecule N.

9. A pharmaceutical composition comprising a MRI detectable species of any one of claims 1 to 5 in an amount sufficient to give the desired level of contrast and at least one pharmaceutically acceptable carrier.

10. A method of imaging organs, tissues, or combinations thereof, comprising administering a composition comprising the MRI detectable species of any one of claims 1 to 5 and imaging the organs, tissues or combinations thereof using nuclear magnetic resonance.

11. A method of diagnosing tumors in an animal, comprising administering a composition comprising the MRI detectable species of any one of claims 1 to 5 and imaging the animal using nuclear magnetic resonance.

12. A process for the preparation of the MRI detectable species of claim 1, said process comprising:
   conjugating the spacer 5, if present, with the nutrient or pseudo-nutrient molecule N and combining the obtained conjugated product with the chelating ligand L; or
   conjugating the chelating ligand L with the spacer 5, if present, and combining the obtained conjugated product with the nutrient or pseudo-nutrient molecule N; and
   metallating the chelating group L of the obtained conjugated compound with the selected paramagnetic metal ion.

* * * * *